(12) United States Patent
Wan et al.

(10) Patent No.: US 12,312,708 B2
(45) Date of Patent: May 27, 2025

(54) APPARATUS AND A METHOD OF DRAWING A FIBRE

(71) Applicant: Agency for Science, Technology and Research, Singapore (SG)

(72) Inventors: Andrew Chwee Aun Wan, Singapore (SG); Du Chan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 506 days.

(21) Appl. No.: 17/625,049

(22) PCT Filed: Jul. 2, 2020

(86) PCT No.: PCT/SG2020/050379
§ 371 (c)(1),
(2) Date: Jan. 5, 2022

(87) PCT Pub. No.: WO2021/006813
PCT Pub. Date: Jan. 14, 2021

(65) Prior Publication Data
US 2022/0282401 A1    Sep. 8, 2022

(30) Foreign Application Priority Data
Jul. 9, 2019    (SG) .......................... 10201906350W

(51) Int. Cl.
*D01D 5/32*    (2006.01)
*A61K 9/50*    (2006.01)
(Continued)

(52) U.S. Cl.
CPC ............. *D01D 5/32* (2013.01); *D01D 5/0046* (2013.01); *D01H 5/72* (2013.01)

(58) Field of Classification Search
CPC ................................ D01D 5/32; D01D 5/0046
See application file for complete search history.

(56) References Cited

U.S. PATENT DOCUMENTS 3,404,433 A * 10/1968 Krutchen ................ B29C 48/05
425/114
4,902,450 A * 2/1990 Morrison .................. B22F 9/08
425/804
(Continued)

FOREIGN PATENT DOCUMENTS

CN    107237005    10/2017

OTHER PUBLICATIONS

Wan A. C. A. et al., Fibers by interfacial polyelectrolyte complexation—processes, materials and applications. Materials Today, Mar. 3, 2016, vol. 19, No. 8, pp. 437-450.
(Continued)

*Primary Examiner* — Emmanuel S Luk
(74) *Attorney, Agent, or Firm* — Kilpatrick Townsend & Stockton LLP

(57) ABSTRACT

There is provided an apparatus for drawing a fibre, the apparatus comprising, a first outlet for dispensing a volume of a first polyionic polymer solution; and a second outlet for dispensing a volume of a second oppositely charged polyionic polymer solution; said second outlet disposed adjacent to the first outlet such that the polymer solutions dispensed therefrom are capable of contacting each other to form a fused droplet comprising a polyelectrolyte complex interface separating the first polyionic and second polyionic polymer solutions; wherein the fused droplet is arranged to move along a fibre drawing path under gravitational force in an opposing direction from the first and second outlets such that nascent fibre is drawn from the polyelectrolyte complex interface. There is also provided a method of drawing the fibre.

20 Claims, 21 Drawing Sheets

(51) Int. Cl.
    *D01D 5/00*      (2006.01)
    *D01D 7/00*      (2006.01)
    *D01F 8/00*      (2006.01)
    *D01H 5/72*      (2006.01)

(56) References Cited

U.S. PATENT DOCUMENTS

| | | | |
|---|---|---|---|
| 5,643,773 A | 7/1997 | Aebischer et al. | |
| 9,663,874 B2* | 5/2017 | Wan | A61L 27/24 |
| 2006/0049542 A1* | 3/2006 | Chu | D01D 4/04 |
| | | | 425/382.2 |
| 2007/0020244 A1* | 1/2007 | Aun Wan | A61L 27/20 |
| | | | 424/443 |
| 2008/0213334 A1 | 9/2008 | Lockwood et al. | |
| 2009/0065969 A1* | 3/2009 | Perera | D01F 8/10 |
| | | | 264/172.15 |
| 2009/0233057 A1* | 9/2009 | Aksay | D01D 5/0038 |
| | | | 427/469 |
| 2016/0319463 A1* | 11/2016 | Park | B82Y 30/00 |
| 2020/0139624 A1* | 5/2020 | Khondoker | B29C 64/118 |
| 2020/0340142 A1* | 10/2020 | Sick | D01D 4/027 |
| 2021/0114276 A1* | 4/2021 | Nelson | B01L 3/502707 |
| 2022/0112626 A1* | 4/2022 | Solberg | D01D 5/0069 |
| 2022/0203278 A1* | 6/2022 | Nakagawa | D04H 1/4258 |

OTHER PUBLICATIONS

International Application No. PCT/SG2020/050379 received an International Search Reportand Written Opinion mailed Jan. 10, 2020, 14 pages.

\* cited by examiner

APPARATUS AND A METHOD OF DRAWING A FIBRE

TECHNICAL FIELD

The present disclosure relates broadly to an apparatus and a method of drawing a fibre.

BACKGROUND

Interfacial Polyelectrolyte Complexation (IPC) is a process by which a fibre can be formed by drawing at an interface between two oppositely charged polyelectrolytes. Typically, polyelectrolyte complexation involves the formation of electrostatic bonds between two polyelectrolytes of opposite charges, leading to a macromolecular complex. During fibre formation using the IPC process, a fibre is drawn from the interface between two oppositely charged polyelectrolytes, where local complexation occurs. During this process, the two water-soluble polyelectrolytes become insolubilized in the form of a polyelectrolyte-complex fibre. It has been shown that the formation of a stable interface is important for continuous fibre formation to occur.

While IPC has been shown to be suitable for various applications, previous work has only been done at the laboratory scale, being restricted by the nature of the process. Typically, the drawing process is performed by using either a pair of forceps, or the tip of a syringe needle that has been made adhesive. After drawing the fibre to a desired length, fibre constructs are made by spooling the fibres using a pitchfork-like apparatus, or wound around polymer film supports. These processes are not easily amenable to a scaled-up process, such as those used in commercial product manufacture.

Thus, there is a need for an apparatus and a method of drawing a fibre that seek to address or at least ameliorate one of the above problems and that are capable of scaling up the formation of IPC fibre constructs.

SUMMARY

In one aspect, there is provided an apparatus for drawing a fibre, the apparatus comprising, a first outlet for dispensing a volume of a first polyionic polymer solution; and a second outlet for dispensing a volume of a second oppositely charged polyionic polymer solution; said second outlet disposed adjacent to the first outlet such that the polymer solutions dispensed therefrom are capable of contacting each other to form a fused droplet comprising a polyelectrolyte complex interface separating the first polyionic and second polyionic polymer solutions; wherein the fused droplet is arranged to move along a fibre drawing path under gravitational force in an opposing direction from the first and second outlets such that nascent fibre is drawn from the polyelectrolyte complex interface.

In one embodiment, the apparatus further comprises, a gas outlet disposed between the first and second outlets, wherein the gas outlet is configured to discharge a stream of gas directed at the fused droplet to initiate movement of the fused droplet along the fibre drawing path.

In one embodiment, the apparatus further comprises, one or more pumps configured to continuously dispense the first and second polyionic polymer solutions via the respective first and second outlets to form additional fused droplets; wherein the additional fused droplets are arranged to move along the fibre drawing path under gravitational force to form additional fibres.

In one embodiment, the apparatus further comprises, a rotatable collector member comprising a contact segment, said contact segment being configured to collect one or more fibres that are detachably coupled to the first and second outlets; wherein the rotatable collector member is configured to rotate in a substantially horizontal plane such that the contact segment is arranged to collect the one or more fibres from the first and second outlets each time the contact segment passes in relation to the first and second outlets; and wherein the rotatable collector member is configured to collect and combine a plurality of fibres to form a fibre construct.

In one embodiment of the apparatus disclosed herein, the rotatable collector member is further configured to wind the fibre or fibre construct onto itself.

In one embodiment, the apparatus further comprises, an elongated guide member coupled to the rotatable collector member and arranged to be substantially aligned with the fibre drawing path, said elongated guide member configured to guide one or more fused droplets lengthwise along the elongated guide member.

In one embodiment, the apparatus further comprises, a first tube comprising a plurality of first outlets defined along a longitudinal axis of the first tube for dispensing a volume of the first polyionic polymer solution, a second tube disposed substantially parallel to the first tube, said second tube comprising a plurality of second outlets defined along a longitudinal axis of the second tube for dispensing a volume of the second polyionic polymer solution; wherein each of the plurality of first outlets is arranged to be disposed adjacent to a second outlet from the plurality of second outlets such that the polymer solutions dispensed therefrom are capable of contacting each other to form a plurality of fused droplets.

In one embodiment, the apparatus further comprises, the first and second outlets in the form of tapered tips; wherein an adhesive substrate is disposed at apex regions of the tapered tips of the first and/or second outlets to facilitate coupling to a starting portion of the fibre; and optionally comprising a tip member disposed between, or in close proximity to, the first and second outlets for coupling to the starting portion of the fibre; and optionally wherein the adhesive substrate is disposed at an apex region of the tip member.

In one embodiment of the apparatus disclosed herein, the first and second polyionic polymers are selected from the following pairs of polycationic and polyanionic polymers consisting of chitosan-alginate, chitosan-heparin, poly(diallyldimethylammonium chloride)-poly(sodium 4-styrenesulfonate), chitosan-carboxymethylcellulose, water-soluble chitin-carboxymethylcellulose, chitosan-gellan and chitosan-poly(glutamic acid).

In one embodiment of the apparatus disclosed herein, the first and/or second polyionic polymer solutions further comprise a biological material; optionally wherein the biological material is arranged to be encapsulated in the fibre as the fibre is being drawn from the polyelectrolyte complex interface; and optionally wherein the biological material is selected from the group consisting of drugs, proteins, DNA, RNA, cells, viruses, microparticles, nanoparticles, contrast agents, and combinations thereof.

In one embodiment, the apparatus further comprises, a third outlet for dispensing a volume of a third polyionic polymer solution having an opposite charge to the second polyionic polymer solution; wherein the third outlet is disposed adjacent to the second outlet such that the third polyionic polymer solution is capable of contacting the second polyionic polymer solution to form a second polyelectrolyte complex interface in the fused droplet; and wherein a combined nascent fibre is drawn from the two polyelectrolyte complex interfaces as the fused droplet is arranged to move along the fibre drawing path.

In one aspect, there is provided a method of drawing a fibre, the method comprising, dispensing a volume of a first polyionic polymer solution from a first outlet; dispensing a volume of a second oppositely charged polyionic polymer solution from a second outlet, said second outlet being disposed adjacent to the first outlet; contacting the volume of the first polyionic polymer solution and the volume of the second polyionic polymer solution to form a fused droplet comprising a polyelectrolyte complex interface separating the first polyionic and second polyionic polymer solutions; moving the fused droplet along a fibre drawing path under gravitational force in an opposing direction from the first and second outlets; and drawing nascent fibre from the polyelectrolyte complex interface.

In one embodiment, the method further comprises, discharging a stream of gas from a gas outlet disposed between the first and second outlets, and directing the stream of gas at the fused droplet to initiate movement of the fused droplet along the fibre drawing path.

In one embodiment, the method further comprises, continuously dispensing the first and second polyionic polymer solutions via the respective first and second outlets using one or more pumps to form additional fused droplets; and moving the additional fused droplets along the fibre drawing path under gravitational force to form additional fibres.

In one embodiment, the method further comprises, rotating a rotatable collector member in a substantially horizontal plane; collecting one or more fibres that are detachably coupled to the first and second outlets using a contact segment of the rotatable collector member each time the contact segment passes in relation to the first and second outlets; and combining a plurality of fibres to form a fibre construct.

In one embodiment, the method further comprises, winding the fibre or fibre construct about the rotatable collector member.

In one embodiment, the method further comprises, guiding one or more fused droplets lengthwise along an elongated guide member coupled to the rotatable collector member and arranged to be substantially aligned with the fibre drawing path.

In one embodiment, the method further comprises, dispensing a volume of the first polyionic polymer solution from a plurality of first outlets defined along a longitudinal axis of a first tube; dispensing a volume of the second polyionic polymer solution from a plurality of second outlets defined along a longitudinal axis of the second tube, said second tube disposed substantially parallel to the first tube; contacting the volume of the first polyionic polymer solution dispensed from each of the plurality of first outlets with the volume of the second polyionic polymer solution from each of the plurality of second outlets to form a plurality of fused droplets.

In one embodiment, the method further comprises, providing the first and second outlets in the form of tapered tips; providing an adhesive substrate disposed at apex regions of the tapered tips of the first and/or second outlets to facilitate coupling to a starting portion of the fibre; and optionally providing a tip member disposed between, or in close proximity to, the first and second outlets; and optionally providing the adhesive substrate disposed at an apex region of the tip member.

In one embodiment of the method disclosed herein, the first and second polyionic polymers are selected from the following pairs of polycationic and polyanionic polymers consisting of chitosan-alginate, chitosan-heparin, poly(diallyldimethylammonium chloride)-poly(sodium 4-styrenesulfonate), chitosan-carboxymethylcellulose, water-soluble chitin-carboxymethylcellulose, chitosan-gellan and chitosan-poly(glutamic acid).

In one embodiment of the method disclosed herein, the first and/or second polyionic polymer solutions further comprise a biological material; optionally wherein the biological material is encapsulated in the fibre as the fibre is being drawn from the polyelectrolyte complex interface; and optionally wherein the biological material is selected from the group consisting of drugs, proteins, DNA, RNA, cells, viruses, microparticles, nanoparticles, contrast agents, and combinations thereof.

In one embodiment, the method further comprises, dispensing a volume of a third polyionic polymer solution from a third outlet disposed adjacent to the second outlet, said third polyionic polymer solution having an opposite charge to the second polyionic polymer solution and; contacting the volume of the third polyionic polymer solution and the volume of the second polyionic polymer solution to form a second polyelectrolyte complex interface in the fused droplet; and drawing a combined nascent fibre from the two polyelectrolyte complex interfaces as the fused droplet is moving along the fibre drawing path.

In one aspect, there is provided a method drawing a fibre, the method comprising, dispensing two or more volumes of polyionic polymer solutions from two or more outlets, respectively, contacting the two or more volumes of polyionic polymer solutions to form a fused droplet comprising at least one polyelectrolyte complex interface, each of the at least one polyelectrolyte complex interface separating two volumes of oppositely charged polyionic polymer solutions; and moving the fused droplet along a fibre drawing path under gravitational force in an opposing direction from the two or more outlets such that nascent fibre is drawn from the at least one polyelectrolyte complex interface.

In one aspect, there is provided an apparatus for drawing a fibre, the apparatus comprising, two or more outlets, each outlet configured for dispensing a volume of a polyionic polymer solution, wherein the two or more outlets are arranged such that the polyionic polymer solutions dispensed therefrom are capable of contacting each other to form a fused droplet comprising at least one polyelectrolyte complex interface, each of the at least one polyelectrolyte complex interface separating two volumes of oppositely charged polyionic polymer solutions; and wherein the fused droplet is arranged to move along a fibre drawing path under gravitational force in an opposing direction from the two or more outlets such that nascent fibre is drawn from the at least one polyelectrolyte complex interface.

In one aspect, there is provided a fibre construct, cell-fibre construct or a food product comprising a plurality of fibres obtained using the method disclosed herein.

Definitions

The term "polyelectrolytes" generally refers to a polymeric compound formed from monomers, each monomer bearing an electrolytic functional group, such as a cationic group. In some instances, the polyelectrolytes are in a solution and is therefore a polymer solution. A polymer solution is charged when the polymer carries a net charge, i.e. either a positive or negative net charge, when present in a solution. Accordingly, the term "oppositely charged" means that one polymer solution carries a net positive charge, while the other polymer solution carries a net negative charge. Since the net charge of the polymer solution is used, the exact value of the charge (expressed for example in Coulomb) is not required. Thus, the net charge is to be understood qualitatively and not quantitatively.

The term "drawing" as defined herein generally refers to an action of extracting or pulling nascent fibre from a polyelectrolyte complex interface. The drawing action may be performed by moving e.g. pulling a point of fibre attachment away from a stationary polyelectrolyte complex interface. The drawing action may also be performed by a moving polyelectrolyte complex interface away from a stationary point of fibre attachment. For example, a fibre drawing tool/device e.g. a prong, a pair of forceps or pipette tip and the like may be used to extract/pull nascent fibre from a polyelectrolyte complex interface via movement of the pair of forceps or pipette tip which is attached to one end of the nascent fibre.

The term "biocompatible" as defined herein includes histocompatible and refers to materials which, when used according to the present disclosure, show low toxicity, acceptable foreign body reactions in the living body, and affinity with living tissues.

The term "biodegradable" as defined herein means that a material or composition will degrade or erode in vivo to form smaller units or chemical species. Degradation can result, for example, from enzymatic, chemical and physical processes.

The term "encapsulate" as defined herein means to entrap biological material within the boundary confines of a fibre matrix.

The term "in vitro" refers to an artificial environment and to processes or reactions that occur within an artificial environment, or elsewhere outside a living organism. In vitro environments may include, but are not limited to, test tubes, cell cultures, bioreactors etc.

The term "in vivo" as used herein refers to the natural environment within the body of an organism (e.g., an animal or a human) and to processes or reaction that occur within a natural environment.

The term "cell culture" as used herein refers to any in vitro culture of cells.

The terms "culture media" as used herein refer to media that are suitable to support the growth of cells of interest in vitro.

The term "substrate" as used herein is to be interpreted broadly to refer to any supporting structure.

The term "layer" when used to describe a first material is to be interpreted broadly to refer to a first depth of the first material that is distinguishable from a second depth of a second material. The first material of the layer may be present as a continuous film, as discontinuous structures or as a mixture of both. The layer may also be of a substantially uniform depth throughout or varying depths. Accordingly, when the layer is formed by individual structures, the dimensions of each of individual structure may be different. The first material and the second material may be same or different and the first depth and second depth may be same or different.

The term "continuous" when used to describe a fibre or fibre construct comprising a plurality of fibres is to be interpreted broadly to refer to a fibre or fibre construct that is substantially without gaps or holes or voids across the length of the fibre or fibre construct. In this regard, a continuous fibre or fibre construct is also intended to include a fibre or fibre construct that may have trivial gaps or holes or voids that may not appreciably affect the desired properties of the fibre or fibre construct. Accordingly, it is also appreciated that the continuous fibre or fibre construct disclosed herein may be formed from very closely and densely packed structures. For instance, the continuous fibre or fibre construct may be grown from densely packed growth sites where each growth site is in proximity or abutting its adjacent growth sites. The continuous layer or continuous film may therefore also be a collection of columnized structures, each columnized structure being grown from each growth site with each columnized structure in proximity or abutting its adjacent columnized structures, thereby forming grain interface or atomic interface therebetween.

The term "micro" as used herein is to be interpreted broadly to include dimensions from about 1 micron to about 1000 microns.

The term "nano" as used herein is to be interpreted broadly to include dimensions less than about 1000 nm.

The term "particle" as used herein broadly refers to a discrete entity or a discrete body. The particle described herein can include an organic, an inorganic or a biological particle. The particle used described herein may also be a macro-particle that is formed by an aggregate of a plurality of sub-particles or a fragment of a small object. The particle of the present disclosure may be spherical, substantially spherical, or non-spherical, such as irregularly shaped particles or ellipsoidally shaped particles. The term "size" when used to refer to the particle broadly refers to the largest dimension of the particle. For example, when the particle is substantially spherical, the term "size" can refer to the diameter of the particle; or when the particle is substantially non-spherical, the term "size" can refer to the largest length of the particle.

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

DETAILED DESCRIPTION

Non-limiting embodiments of an apparatus and a method of drawing a fibre are disclosed hereinafter.

In various embodiments, an apparatus for drawing a fibre is provided. The apparatus for drawing a fibre may utilise an IPC process. Polyelectrolyte complexation involves the formation of electrostatic bonds between oppositely charged polyelectrolytes, leading to a macromolecular complex. During fibre formation using the IPC process, a fibre is drawn from the interface between oppositely charged polyelectrolytes, where local complexation occurs. During this process, the water-soluble polyelectrolytes become insolubilised in the form of a polyelectrolyte-complex fibre.

In various embodiments, the apparatus for drawing a fibre comprises two or more outlets. Each of the two or more outlets is configured for dispensing a volume of a polyionic polymer solution, e.g. a polyanionic polymer or polycationic polymer solution. The two or more outlets may be arranged such that the polyionic polymer solutions dispensed therefrom are capable of contacting each other to form a fused droplet at an initial position. The initial position may be a region where the polyionic polymer solutions exit from the respective outlets. The two or more outlets may further be arranged such that any two polyionic polymer solutions contacting each other in the fused droplet are oppositely charged. The two oppositely charged polyionic polymer solutions contacting each other form a polyelectrolyte complex interface which separates the two volumes of oppositely charged polyionic polymer solutions. The fused droplet may comprise at least one polyelectrolyte complex interface. The fused droplet is arranged to move along a fibre drawing path under gravitational force in an opposing direction from the two or more outlets such that nascent fibre is drawn from the at least one polyelectrolyte complex interface. In various embodiments, where nascent fibre is drawn from more than one polyelectrolyte complex interface using the apparatus and method as disclosed herein, such a technique is termed "rolling droplet-multi interfacial polyelectrolyte complexation (RD-MIPC)".

In various embodiments, the apparatus for drawing a fibre comprises a first outlet for dispensing a volume of a first polyionic polymer solution e.g. polyanionic polymer (i.e. polyelectrolyte) solution and a second outlet for dispensing a volume of a second polyionic polymer solution e.g. polycationic polymer (i.e. polyelectrolyte) solution. The second outlet may be arranged to be disposed adjacent to the first outlet such that the polyanionic and polycationic polymer solutions dispensed therefrom are capable of contacting each other to form a fused droplet at an initial position. The initial position may be a region where the polyanionic and polycationic polymer solutions exit from the respective first and second outlets. In one embodiment, the first and second outlets are spaced apart such that there is no physical contact between the first and second outlets. In another embodiment, the first and second outlets are abutting each other such that there is physical contact between the first and second outlets. The first and second outlets may be in the form of a tip e.g. tapered tip such as a pipette tip or tip of a syringe needle.

In various embodiments, the fused droplet comprises a polyelectrolyte complex interface separating the polyanionic and polycationic polymer solutions. The polyelectrolyte complex interface functions as a barrier which prevents free mixing of the polyanionic and polycationic polymer solutions and is a pre-requisite for IPC fibre formation. The first and second outlets are respectively arranged to dispense an increasing volume of the polyanionic and polycationic polymer solutions to the fused droplet to trigger movement of the fused droplet along a fibre drawing path. As the volume of the fused droplet exceeds a critical/threshold level, the gravitational force acting on the fused droplet exceeds the mutual adhesive/attractive forces e.g. surface tension that are holding the fused droplet to the initial position. Consequently, the fused droplet can no longer be held by the mutual adhesive/attractive forces e.g. surface tension at the initial position and moves away from the first and second outlets under gravitational force.

In various embodiments, the fused droplet is arranged to move along the fibre drawing path under gravitational force in an opposing direction from the first and second outlets, such that nascent fibre is drawn from the polyelectrolyte complex interface. That is, the fibre (i.e. polyelectrolyte complex fibre) is drawn from the polyelectrolyte complex interface as the fused droplet comprising the polyelectrolyte complex interface is moving away e.g. falling/travelling downwards from the initial position where the fused droplet was first formed. The drawing action due to the moving fused droplet disrupts the polyelectrolyte complex interface, leading to scattered domains of complexation that act as fibre nucleation sites, "nuclear fibres" grow by depleting the surrounding polyelectrolyte solution, resulting in a decrease in its viscosity, and finally, these "nuclear fibres" coalesce, leading to formation of a thicker primary fibre comprising submicron nuclear fibres and gel droplets (beads) along its axis, that becomes protuberances upon drying. In various embodiments, two or more fibres (i.e. polyelectrolyte complex fibres) may be collected and fused together to form a fibre construct, prior to drying. As a result, the protuberances due to the gel droplets may not be formed. In various embodiments, where nascent fibre is drawn from a single polyelectrolyte complex interface using the apparatus and method as disclosed herein, such a technique is termed as "rolling droplet-interfacial polyelectrolyte complexation (RD-IPC)".

In various embodiments, the apparatus for drawing a fibre may further comprise a third outlet for dispensing a volume of a third polyionic polymer solution. The third outlet may be arranged in series with the first and second outlets. For example, the third outlet may be disposed adjacent to (e.g. spaced apart or abutting) the second outlet such that the third polyionic polymer solution is capable of contacting the second polyionic polymer solution (which has an opposite charge to the third polyionic polymer solution) to form a polyelectrolyte complex interface in the fused droplet. In this arrangement, the volume e.g. droplet of second polyionic polymer solution e.g. polycationic polymer solution dispensed from the second outlet may be viewed as a central droplet which is flanked by volumes e.g. droplets of oppositely charged polyionic polymer solutions e.g. polyanionic polymer solutions dispensed from the adjacent first and third outlets. The first polyionic polymer solution e.g. polyanionic polymer solution from the first outlet is arranged to form a first polyelectrolyte complex interface with the second polyionic polymer solution e.g. polycationic polymer solution from the second outlet. The third polyionic polymer solution e.g. polyanionic polymer solution from the third outlet is arranged to form a second polyelectrolyte complex interface with the second polyionic polymer solution e.g. polycationic polymer solution from the second outlet. The first and second polyelectrolyte complex interfaces are disposed on opposite sides of the central droplet. The polyionic polymer e.g. polyanionic polymer solutions from the first and third outlets may comprise the same or different polyanionic polymers. The fused droplet comprising the two polyelectrolyte complex interfaces is arranged to move along the fibre drawing path under gravitational force in an opposing direction from the three outlets such that nascent fibre is drawn from both polyelectrolyte complex interfaces. The nascent fibre may be a combined/composite fibre formed from two component fibres, each drawn from the respective first and second polyelectrolyte complex interfaces.

It will be appreciated that for the case where the first and third polyionic polymer solutions comprise different polyanionic polymers and/or components, the nascent fibre e.g. composite/combined fibre drawn from the first and second polyelectrolyte complex interfaces may comprise two distinct components, i.e. one component having characteristics of the first polyelectrolyte complex interface formed by the first and second polyionic polymers, another component having characteristics of the second polyelectrolyte complex interface formed by the second and third polyionic polymers. This advantageously allows a fibre to have a combination of desired properties by selecting an appropriate set of polyionic polymers and/or components for fibre drawing.

It will be appreciated that the charge of the polyionic polymer solution dispensed from each outlet is not limited to the above example embodiment. In another example, the first and third outlets may be arranged to dispense polycationic polymer solutions and the second outlet may be arranged to dispense a polyanionic polymer solution.

It will also be appreciated that the above example using three outlets is for illustration purposes only, and that the apparatus and method as disclosed herein may be capable of employing more than three outlets for drawing fibres. For example, other MIPC droplet configurations, e.g. a triangular or square configuration may be employed.

In a triangular configuration, a first outlet, a second outlet and a third outlet may be arranged to form the three points/vertices of a triangle e.g. an equilateral triangle. A fourth outlet may be positioned at the centre region of the triangle such that polyionic polymer solutions dispensed from the first, second and third outlets are each capable of forming a polyelectrolyte complex interface with polyionic polymer solution dispensed from the fourth outlet. The polyionic polymer solutions dispensed from the first, second and third outlets are oppositely charged from the polyionic polymer solution dispensed from the fourth outlet. Three polyelectrolyte complex interfaces may be formed in the triangular configuration.

In a square configuration, a first outlet, a second outlet, a third outlet and a fourth outlet may be arranged to form the four points/corners of a square. A fifth outlet may be positioned at the centre region of the square such that polyionic polymer solutions dispensed from the first, second, third and fourth outlets are each capable of forming a polyelectrolyte complex interface with polyionic polymer solution dispensed from the fifth outlet. The polyionic polymer solutions dispensed from the first, second, third and fourth outlets are oppositely charged from the polyionic polymer solution dispensed from the fifth outlet. Four polyelectrolyte complex interfaces may be formed in the square configuration.

In various embodiments, the process of drawing a fibre is capable of being performed at room temperature (e.g. 25° C.) and using aqueous solutions having near-neutral pH (e.g. pH 7). This advantageously enables incorporation and immobilisation of biological material such as proteins, and to encapsulate cells. The apparatus for implementing the IPC process as disclosed herein may be capable of continuously drawing fibres as oppositely charged polyelectrolyte solutions are continuously dispensed from the respective outlets. This provides a significant advantage over conventional IPC process whereby fibres are drawn from a discrete stationary droplet, and fibre drawing would stop once the polyelectrolyte in the droplet is used up.

In various embodiments, the apparatus for drawing a fibre further comprises a tip member disposed between, or in close proximity to, the outlets e.g. first and second outlets. For example, the tip member may be in close proximity by being disposed in a region of space below the first and/or second outlet. The tip member may also be in close proximity by being disposed adjacent to either the first outlet or the second outlet. The tip member comprises a substrate e.g. an adhesive substrate disposed at its apex region which functions to attach to a starting portion of the fibre at the initial position. As the volume of the fused droplet exceeds the critical/threshold level, a nascent starting portion of the fibre is drawn from the polyelectrolyte complex interface as the fused droplet begins to fall from the initial position. The starting portion of the fibre is attached to the first and second outlets as the fibre continues to be generated from the polyelectrolyte complex interface of the moving fused droplet. In this respect, the tip member may reinforce attachment of the starting portion of the fibre to the first and second outlets.

The adhesive substrate may also be disposed at the outlet for dispensing polyelectrolyte solution e.g. the first outlet for dispensing the polyanionic polymer solution and/or the second outlet for dispensing the polycationic polymer solution. For example, where the first and second outlets are in the form of a tapered tip, the adhesive substrate may be disposed at the apex regions of the tapered tips of the first outlet and/or second outlet. The adhesive substrate may be applied as a coating to the outlet for dispensing polyelectrolyte solution and the tip member. The adhesive substrate functions to facilitate nascent fibre attachment to the outlets e.g. first and/or second outlets and optionally, the tip member.

In various embodiments, the adhesive may be any material capable of maintaining contact (directly or indirectly) between the outlet/tip member and each polyelectrolyte solution. The adhesive substrate may comprise organic and/or inorganic materials. Suitable organic adhesives include but are not limited to fibrin glue, polyvinylpyrolidone, polyvinylpyrolidone/vinyl acetate copolymers, cyanoacrylate gel, platelated gel, chitosan or gelatin-resorcin-formaldehyde (GRFG), organic polymeric compositions represented by the group of alkyd resins, polyvinyl acetaldehydes, polyvinyl alcohols, polyvinyl acetates, poly(ethylene oxide), polyacrylates, ketone resins, polyvinylpyrolidone, polyvinylpyrrolidone/vinyl acetate copolymer, polyethylene glycols of 200 to 1000 molecular weight and polyoxyethylene/polyoxopropylene block copolymers (Polyox), silicone resins and silicone based pressure sensitive adhesives.

In various embodiments, the apparatus for drawing a fibre further comprises a gas outlet for discharging a stream of gas to dislodge the fused droplet from its initial position, thereby initiating or triggering movement of the fused droplet along the fibre drawing path. The gas outlet may be disposed near the outlets for dispensing polyionic polymer solutions. For example, the gas outlet may be disposed between the first outlet for dispensing the polyanionic polymer solution and the second outlet for dispensing the polycationic polymer solution. The gas outlet may be an open end of a tubing, said tubing having another end connected to a gas source e.g. tank/cannister/cylinder for storing the gas. The gas may be an inert gas such as nitrogen, helium, hydrogen, and argon. In one embodiment, the gas is nitrogen. In various embodiments, the gas outlet is arranged such that gas discharged from the gas outlet is directed at the initial position where the fused droplet is formed, to initiate or trigger movement of the fused droplet along the fibre drawing path.

It will be appreciated that in the apparatus and method as disclosed herein, the initial release of the fused droplet depends on its weight, as the fused droplet has to be sufficiently heavy to overcome its adhesion to the dispensing outlets e.g. pipette tips. In general, the size of a fused droplet determines the size of the polyelectrolyte complex interface, which in turn determines the thickness of the fibre. Typically, relatively thicker fibres (e.g. with a diameter of more than about 6 μm) may be achieved by combining fibres or by increasing the viscosity of the polyionic polymer solutions. Fibres with relatively smaller fibre diameters or thicknesses (e.g. with a diameter of about 6 μm or less) may be obtained by drawing fibres from a fused droplet with a relatively smaller size. For example, a stream of gas may be directed at the fused droplet at the initial position at appropriate timings/instances to push away or dislodge the fused droplet from its initial position or attachment point before it achieves the critical weight to move along the fibre drawing path under gravitational force alone. In this way, smaller fibre diameters (e.g. with a diameter of less than about 6 μm) may be achieved. In various embodiments, where a gas outlet is used to initiate or trigger movement of the fused droplet along the fibre drawing path using the apparatus and method as disclosed herein, such a technique is termed as "assisted RD-IPC" and "assisted RD-MIPC".

In various embodiments, the apparatus for drawing a fibre further comprises reservoirs for holding/storing the polyanionic and polycationic polymer solutions. The reservoir may be in the form of a container such as a test tube, beaker, or tank for holding various volumes (e.g. in the order of millilitres to litres), depending on the scale of production. The reservoirs may be coupled to the first and second outlets via tubings. In one embodiment, the apparatus may comprise a first reservoir coupled to the first outlet, said first reservoir being configured for holding the polyanionic polymer solution; and a second reservoir coupled to the second outlet, said second reservoir being configured for holding the polycationic polymer solution.

In various embodiments, the apparatus for drawing a fibre further comprises one or more pumps being configured for continuously dispensing the polyanionic and polycationic polymer solutions via the respective first and second outlets. Continuous dispensing of the polyanionic and polycationic polymer solutions via the respective first and second outlets results in the volume of the fused droplet exceeding the critical/threshold level, thereby triggering movement of the fused droplet along the fibre drawing path. Continuous dispensing of the polyanionic and polycationic polymer solutions via the respective first and second outlets also results in the formation of additional fused droplets which are arranged to move along the fibre drawing path under gravitational force to form additional fibres. Examples of pumps for dispensing the solutions may include but are not limited to a syringe pump, pneumatic pump and peristaltic pump. The pump may be adjusted to control the flow rate of the polyanionic and polycationic polymer solutions to be dispensed via the respective first and second tips. Advantageously, the apparatus is capable of continuously providing polyelectrolyte solutions such that fibres manufactured by the apparatus may possess substantially uniform diameters.

In various embodiments, the polyanionic and polycationic polymer solutions may be arranged to be dispensed at a flow rate of from about 1 μL/min to about 1000 μL/min, from about 5 μL/min to about 950 μL/min, from about 10 μL/min to about 900 μL/min, from about 20 μL/min to about 850 μL/min, from about 30 μL/min to about 800 μL/min, from about 40 μL/min to about 750 μL/min, from about 50 μL/min to about 700 μL/min, from about 60 μL/min to about 650 μL/min, from about 70 μL/min to about 600 μL/min, from about 80 μL/min to about 550 μL/min, from about 90 μL/min to about 500 μL/min, from about 100 μL/min to about 450 μL/min, from about 150 μL/min to about 400 μL/min, from about 200 μL/min to about 350 μL/min, or from about 250 μL/min to about 300 μL/min. In one embodiment, the polyanionic and polycationic polymer solutions are arranged to be dispensed at a flow rate of from about 50 μL/min to about 100 μL/m in.

In various embodiments, the fused droplet comprising the polyelectrolyte complex interface is arranged to travel downwards from the initial position under the influence of gravity. The fibre that is being drawn from the polyelectrolyte complex interface may be lengthening at a rate of from about 5 mm/second to about 200 mm/second, from about 10 mm/second to about 195 mm/second, from about 15 mm/second to about 190 mm/second, from about 20 mm/second to about 185 mm/second, from about 25 mm/second to about 180 mm/second, from about 30 mm/second to about 175 mm/second, from about 35 mm/second to about 170 mm/second, from about 40 mm/second to about 165 mm/second, from about 45 mm/second to about 160 mm/second, from about 50 mm/second to about 155 mm/second, from about 55 mm/second to about 150 mm/second, from about 60 mm/second to about 145 mm/second, from about 65 mm/second to about 140 mm/second, from about 70 mm/second to about 135 mm/second, from about 75 mm/second to about 130 mm/second, from about 80 mm/second to about 125 mm/second, from about 85 mm/second to about 120 mm/second, from about 90 mm/second to about 115 mm/second, from about 95 mm/second to about 110 mm/second, or from about 100 mm/second to about 105 mm/second. In one embodiment, the fibre that is being drawn from the polyelectrolyte complex interface is lengthening at a rate of about 40 mm/second.

In various embodiments, continuous flow of the polyanionic and polycationic polymer solutions results in the formation of more/additional fused droplets, which are arranged to successively roll down existing fibres drawn from earlier fused droplets. The additional fused droplets are arranged to draw additional fibres parallel to the existing fibres such that the additional fibres fuse with existing fibres to form a fibre construct comprising a plurality of fibres. As the number of fibres increases, the thickness or diameter of the fibre construct also increases. This provides a significant advantage over conventional IPC processes whereby there is limited control over the fibre diameter In various embodiments, the fibre construct comprises from about 2 to about 1000 fibres, from about 3 to about 950 fibres, from about 5 to about 900 fibres, from about 10 to about 850 fibres, from about 20 to about 800 fibres, from about 30 to about 750 fibres, from about 40 to about 700 fibres, from about 50 to about 650 fibres, from about 60 to about 600 fibres, from about 70 to about 550 fibres, from about 80 to about 500 fibres, from about 90 to about 450 fibres, from about 100 to about 400 fibres, from about 150 to about 350 fibres, from about 200 to about 300 fibres, or from about 250 to about 300 fibres.

In various embodiment, the fibre has a substantially homogenous diameter along its length. Each fibre may have an average diameter ranging from about 1 µm to about 200 µm, from about 5 µm to about 195 µm, from about 10 µm to about 190 µm, from about 15 µm to about 185 µm, from about 20 µm to about 180 µm, from about 25 µm to about 175 µm, from about 30 µm to about 170 µm, from about 35 µm to about 165 µm, from about 40 µm to about 160 µm, from about 45 µm to about 155 µm, from about 50 µm to about 150 µm, from about 55 µm to about 145 µm, from about 60 µm to about 140 µm, from about 65 µm to about 135 µm, from about 70 µm to about 130 µm, from about 75 µm to about 125 µm, from about 80 µm to about 120 µm, from about 85 µm to about 115 µm, from about 90 µm to about 110 µm, from about 95 µm to about 105 µm, or from about 100 µm to about 105 µm. It will be appreciated that the thickness/diameter of a fibre depends on parameters such as the concentration of the polyelectrolyte solutions. It will also be appreciated that fibres may be combined to form a thicker fibre construct.

In various embodiments, each fibre may have a length ranging from about 1 mm to about 1000 mm, from about 10 mm to about 950 mm, from about 25 mm to about 900 mm, from about 50 mm to about 850 mm, from about 100 mm to about 800 mm, from about 150 mm to about 750 mm, from about 200 mm to about 700 mm, from about 250 mm to about 650 mm, from about 300 mm to about 600 mm, from about 350 mm to about 550 mm, from about 400 mm to about 500 mm, or from about 400 mm to about 450 mm. In one embodiment, each fibre has a length of about 500 mm.

In various embodiments, the apparatus for drawing a fibre further comprises a collector module for collecting and accumulating the fibres. The collector module functions to collect the fibre by detaching the fibre from the first and second outlets at the initial position and transferring the detached fibre to a separate location where a plurality of detached fibres is being accumulated. The fibre may be detached from the initial position even while the fibre is still being drawn from the polyelectrolyte complex interface of the fused droplet moving along the fibre drawing path.

In various embodiments, the collector module comprises a rotatable collector member. The rotatable collector member may comprise one or more contact segments. Each contact segment may be configured to collect one or more fibres that are detachably coupled to the first and second outlets. The rotatable collector member may be disposed in proximity to the first and second outlets and may be configured to rotate in a plane e.g. a substantially horizontal plane such that the contact segment is arranged to collect one or more fibres from the first and second outlets each time the contact segment passes in relation to e.g. under the first and second outlets. The rotatable collector member may be configured to collect and combine a plurality of fibres to form a fibre construct.

In various embodiments, the collector module may comprise a support member configured to rotate about its vertical axis which is substantially parallel to the vertical axis of the apparatus. The support member may be coupled to a motor for rotating the support member about the vertical axis of the support member. The rotatable collector member may be mounted on the support member such that the rotatable collector member is capable of being rotated about the vertical axis of the support member. The rotatable collector member functions to detach the fibre from the first and second outlets at the initial position while being rotated about the vertical axis. The collector module may further comprise a rotatable base member e.g. base plate mounted on the support member, said rotatable base member being disposed directly below the rotatable collector member. The rotatable base member functions to attach to a terminal end portion of the fibre. In one embodiment, the rotatable collector member is a rectangular sheet with one end mounted on the support member and with its planar surface being substantially parallel to the vertical plane. In one embodiment, the rotatable base member is a rectangular base with its planar surface being substantially parallel to the horizontal plane (i.e. ground).

In various embodiments, the collector module further comprises a guide member e.g. elongated guide member such as a stainless-steel rod coupled to the rotatable collector member. The guide member may be oriented to be aligned with the fibre drawing path e.g. substantially parallel to the vertical axis and may be arranged to guide the moving fused droplet along the length of the guide member. The fibre drawn from the fused droplet may adhere to the guide member as the fused droplet moves e.g. rolls down along the guide member.

During operation, a nascent starting portion of the fibre is drawn from the polyelectrolyte complex interface as the fused droplet begins to move along the fibre drawing path away from the first and second outlets. Due to its rotating motion, the rotatable collector member detaches a first fibre from the first and second outlets at the initial position where the fused droplet was formed, as the rotatable collector member passes in relation to e.g. under the initial position. As the collector member continues rotating about the vertical axis of the support member, the first fibre continues to increase in length due to the moving fused droplet along its fibre drawing path, until the fused droplet reaches the rotatable base member and the terminal end portion of the fibre attaches to the rotatable base member. As the rotatable collector member passes under the first and second outlets for a second and subsequent times, a second and subsequent fibres are detached from the first and second outlets and are combined with the first fibre. With each cycle of rotation, an additional fibre is deposited and combined to existing fibres, thereby forming a fibre construct having a plurality of fibres.

In various embodiments, the rotatable collector member is a spool or is configured to function as a spool for winding the fibre or fibre construct thereon. After a fibre or a fibre construct having a plurality of fibres is formed, the rotatable collector member may be arranged to rotate about a horizontal axis of rotation such that the fibre or fibre construct is wound around the rotatable collector member.

It will be appreciated that the above description of the collector module with reference to a RD-IPC technique is for illustrative purposes, the collector module may also be applicable for a RD-MIPC technique.

In various embodiments, the apparatus for drawing a fibre further comprises a first tube having a plurality of first outlets defined along a longitudinal axis of the first tube for dispensing a volume of the polyanionic polymer solution, and a second tube having a plurality of second outlets defined along a longitudinal axis of the second tube for dispensing a volume of the polycationic polymer solution. The first and second tubes may be arranged to be disposed substantially parallel to each other, such that each of the plurality of first outlets is arranged to be positioned adjacent to/in close proximity to a second outlet from the plurality of second outlets. Such a configuration provides drawing of multiple fibres simultaneously and advantageously enables mass production of fibres and fibre constructs. It will be appreciated that this configuration may be combined with the collector module as disclosed herein to from multiple fibre constructs in series.

In various embodiments, the polyanionic polymer solution comprises one or more polyanionic polymer selected from the group consisting of natural and synthetic carbohydrate or polypeptide polymers having a net negative charge. Polymers that have a net negative charge include, but are not limited to, alginate, gellan, chondroitin sulphate, hyaluronic acid, polyglutamic acid, fibrinogen; terpolymer consisting of methyl methacrylate, hydroxyethyl methacrylate and methacrylic acid; carboxymethylated, phosphorylated and/or sulfated derivatives, which includes those of cellulose, chitin and chitosan; deoxyribonucleic acid (DNA), ribonucleic acid (RNA) and their derivatives; natural and synthetic carbohydrates having a net negative charge; polypeptide polymers having a net negative charge; or combinations thereof.

In various embodiments, the polyanionic polymer solution may have a polyanionic polymer concentration ranging from about 0.1% (w/v) to about 10% (w/v), from about 0.2% (w/v) to about 9.5% (w/v), from about 0.3% (w/v) to about 9% (w/v), from about 0.4% (w/v) to about 8.5% (w/v), from about 0.5% (w/v) to about 8% (w/v), from about 0.6% (w/v) to about 7.5% (w/v), from about 0.7% (w/v) to about 7% (w/v), from about 0.8% (w/v) to about 6.5% (w/v), from about 0.9% (w/v) to about 6% (w/v), from about 1% (w/v) to about 5.5% (w/v), from about 1.5% (w/v) to about 5% (w/v), from about 2% (w/v) to about 4.5% (w/v), from about 2.5% (w/v) to about 4% (w/v), or from about 3% (w/v) to about 3.5% (w/v).

In various embodiments, the polycationic polymer solution comprises one or more polycationic polymer selected from the group consisting of natural and synthetic carbohydrate or polypeptide polymers having a net positive charge. Polymers that have a net positive charge include, but are not limited to, chitin, chitosan, poly(lysine), poly(arginine), polyornithine, polyethyleneimine; galactosylated compounds of chitin, collagen, chitosan and methylated collagen; natural and synthetic carbohydrates having a net positive charge; polypeptide polymers having a net positive charge; or combinations thereof.

In various embodiments, the polycationic polymer solution may have a polycationic polymer concentration ranging from about 0.1% (w/v) to about 10% (w/v), from about 0.2% (w/v) to about 9.5% (w/v), from about 0.3% (w/v) to about 9% (w/v), from about 0.4% (w/v) to about 8.5% (w/v), from about 0.5% (w/v) to about 8% (w/v), from about 0.6% (w/v) to about 7.5% (w/v), from about 0.7% (w/v) to about 7% (w/v), from about 0.8% (w/v) to about 6.5% (w/v), from about 0.9% (w/v) to about 6% (w/v), from about 1% (w/v) to about 5.5% (w/v), from about 1.5% (w/v) to about 5% (w/v), from about 2% (w/v) to about 4.5% (w/v), from about 2.5% (w/v) to about 4% (w/v), or from about 3% (w/v) to about 3.5% (w/v). In one embodiment, the polycationic polymer solution comprises water-soluble chitin from about 0.2% (w/v) to about 2% (w/v).

It will be appreciated that a minimum concentration of polyelectrolytes plays a role in enabling continuous IPC fibre drawing. In general, higher molecular weight polyelectrolytes draw better due to their ability to form a viscous complex that stabilises the polyelectrolyte complex interface. The effect of molecular weight can also be explained by the fact that at higher molecular weight, polyelectrolytes have a larger area and segments that can support interaction and facilitate complexation. It will also be appreciated that fibre drawing rate plays a role in enabling continuous IPC fibre drawing. Fibre drawing should be slow enough to create a stable IPC fibre, a process which is likely related to the replacement at the interface with fresh polyelectrolytes through diffusion and convection. Slower drawing rates may be applicable for more viscous solutions, where diffusion rates are relatively slower. In one embodiment, the polyanionic polymer solution is sodium alginate and the polycationic polymer solution is chitosan or water-soluble chitin. In one embodiment, IPC fibres can be prepared from about 1% (w/v) chitosan and about 0.5% (w/v) alginate at a flow rate of about 25 µL/min. In another embodiment, IPC fibres can be prepared from about 1% (w/v) water-soluble chitin and about 3% (w/v) RGD-alginate at a flow rate of about 90 µL/min. In yet another embodiment, IPC fibres can be prepared from about 1% (w/v) water-soluble chitin and about 1% alginate at a flow rate of about 120 µL/min.

It will be appreciated that other combinations of polyelectrolytes apart from chitin and RGD-alginate may be used to draw IPC fibres. Some examples of polyelectrolyte combinations for drawing IPC fibres using the apparatus and method as disclosed herein may include but are not limited to chitosan-heparin, poly(diallyldimethylammonium chloride)-poly(sodium 4-styrenesulfonate), chitosan-carboxymethylcellulose, water-soluble chitin-carboxymethylcellulose, chitosan-gellan and chitosan-poly(glutamic acid). In one example embodiment, the combination of polyionic polymers is selected from the following pairs of polycationic and polyanionic polymers consisting of chitosan-alginate, chitosan-heparin, poly(diallyldimethylammonium chloride)-poly(sodium 4-styrenesulfonate), chitosan-carboxymethylcellulose, water-soluble chitin-carboxymethylcellulose, chitosan-gellan and chitosan-poly(glutamic acid).

In various embodiments, the polyanionic polymer and/or polycationic polymer are biodegradable and/or biocompatible. In various embodiments, the polyanionic polymer solution and/or polycationic polymer solution further comprise a biological material. It will be appreciated that the types of biological material comprised in the polymer solutions are essentially unlimited as long as they are compatible with the polymer solutions used. For example, the biological material may include edible materials such as animal and plant proteins, lipids, polysaccharides, dietary fibres, vitamins, minerals, cells and cellular components. In another example, the biological material may be selected from the group consisting of drugs, proteins, DNA, RNA, cells, viruses, microparticles, nanoparticles, contrast agents, and combinations thereof. The cells may include prokaryotic cells and eukaryotic cells which are either naturally occurring or genetically engineered, parts of cells such as mitochondria and protoplasts or any other naturally occurring or engineered biological material. The genetically engineered cells may include, but are not limited to, fused cells such as hybridoma cells or genetically modified cells produced, e.g., by recombinant technology.

In various embodiments, the biological material may be arranged to be encapsulated in the fibre as the fibre is being drawn from the polyelectrolyte complex interface. That is, when the polymer solution comprises biological material, drawing a fibre from the polyelectrolyte complex interface would simultaneously draw the biological material from the polyanionic and/or polycationic polymer solutions. The biological material may thus be encapsulated within the matrix of the drawn fibre. Alternatively, the biological material may also be comprised in a separate polyelectrolyte solution which can be coated as a layer onto the surface of a drawn fibre/fibre construct. In one embodiment, skeletal muscle cells such as myoblasts may be encapsulated in the fibres and are capable of maintaining its viability while being cultured in the fibres.

In various embodiments, a method of drawing a fibre is provided. The method comprises dispensing two or more volumes of polyionic polymer solutions from two or more outlets, respectively. For example, the method may comprise dispensing three volumes of polyionic polymer solutions from three outlets, respectively. In one example, two of the polyionic polymer solutions may be polycationic polymer solutions and one of the polyionic polymer solutions may be a polyanionic polymer solution. In another example, two of the polyionic polymer solutions may be polyanionic polymer solutions and one of the polyionic polymer solutions may be a polycationic polymer solution. The method further comprises contacting the two or more volumes of polyionic polymer solutions to form a fused droplet comprising at least one polyelectrolyte complex interface. Each polyelectrolyte complex interface is formed by two volumes of oppositely charged polyionic polymer solutions and the polyelectrolyte complex interface acts as a barrier separating the two volumes of oppositely charged polyionic polymer solutions. The method further comprises moving the fused droplet along a fibre drawing path under gravitational force in an opposing direction from the two or more outlets such that nascent fibre is drawn from the at least one polyelectrolyte complex interface.

In various embodiments, the method of drawing a fibre comprises dispensing a volume of a first polyionic polymer solution e.g. polyanionic polymer solution from a first outlet and dispensing a volume of a second polyionic polymer solution e.g. polycationic polymer solution from a second outlet. The volume of polyanionic polymer solution and the volume of polycationic polymer solution are contacted at an initial position near the first and second outlets to form a fused droplet comprising a polyelectrolyte complex interface separating the polyanionic and polycationic polymer solutions. The method further comprises a step of drawing the fibre from the polyelectrolyte complex interface by moving the fused droplet along a fibre drawing path under gravitational force in an opposing direction from the first and second outlets.

In various embodiments, the method of drawing a fibre may further comprise dispensing a volume of a third polyionic polymer solution from a third outlet disposed adjacent to the second outlet. The third outlet may be arranged in series with the first and second outlets such that the first and third outlets are disposed on opposite sides of the second outlet. The third polyionic polymer solution has an opposite charge to the second polyionic polymer solution. The method further comprises contacting the volume of the third polyionic polymer solution and the volume of the second polyionic polymer solution to form a second polyelectrolyte complex interface in the fused droplet. It will be appreciated that the second polyelectrolyte complex interface is distinct from the first polyelectrolyte complex interface formed between the first polyionic polymer solution e.g. polyanionic polymer solution from the first outlet and the second polyionic polymer solution e.g. polycationic polymer solution from the second outlet. The polyionic polymer e.g. polyanionic polymer solutions from the first and third outlets may comprise the same or different polyanionic polymers. The method further comprises drawing a combined nascent fibre from the two polyelectrolyte complex interfaces as the fused droplet is moving along the fibre drawing path under gravitational force in an opposing direction from the three outlets. It will also be appreciated that the above example using three outlets is for illustration purposes only, and that the method as disclosed herein may be capable of employing more than three outlets for drawing fibres.

In various embodiments, the method further comprises dispensing an increasing volume of the polyanionic and polycationic polymer solutions to the fused droplet to trigger movement of the fused droplet along the fibre drawing path e.g. to cause the fused droplet to travel downwards away from the first and second outlet. As the volume of the fused droplet increases beyond a critical/threshold level, the gravitational forces acting on the fused droplet exceeds the adhesive/attractive forces e.g. surface tension that are holding the fused droplet at the initial position. Consequently, the fused droplet falls downwards from the initial position under the influence of gravity.

In various embodiments, the method further comprises coupling a starting portion of the fibre to a substrate e.g. adhesive substrate disposed at an apex region of a tip member. This may reinforce the attachment of the starting portion of the fibre to the first and second outlets as the fused droplet is moving further away from the first and second outlets and causing the fibre to be drawn from the polyelectrolyte complex interface. The adhesive substrate may also be provided at the outlet for dispensing polyelectrolyte solution e.g. the first outlet for dispensing the polyanionic polymer solution and/or the second outlet for dispensing the polycationic polymer solution, to facilitate coupling to a starting portion of the fibre.

In various embodiments, the method further comprises discharging a stream of gas from a gas outlet and directing the stream of gas at the fused droplet to initiate movement of the fused droplet along the fibre drawing path. The gas outlet may be disposed near the outlets for dispensing polyionic polymer solutions, e.g. between the first and second outlets.

In various embodiments, the method further comprises continuously dispensing and contacting the polyanionic and polycationic polymer solutions using one or more pumps to form one or more additional fused droplets. As each of the one or more additional droplets increases in mass and volume beyond the critical/threshold level, the one or more additional droplets is triggered to move along the fibre drawing path by e.g. rolling downwards in a successive manner along an earlier formed fibre to form one or more additional fibres. The one or more additional fibres may fuse to the earlier drawn fibre to form a fibre construct comprising a plurality of fused fibres.

In various embodiments, the method further comprises detaching a plurality of fibres from the initial position while each of the plurality of fibres is still being drawn from the polyelectrolyte complex interface. The plurality of detached fibres is collected and fused together to form a fibre construct.

In various embodiments, the method further comprises winding the fibre or fibre construct around a spool. The fibre or fibre construct may contain biological material such as cells encapsulated within the fibre or fibre construct. The fibre or fibre construct may be wound to form a scaffold or matrix for culturing the encapsulated cells.

In various embodiments, the step of dispensing the polyanionic and polycationic polymer solutions is performed at a flow rate of from about 1 μL/min to about 1000 μL/min. In various embodiments, the step of drawing the fibre is performed at a rate of from about 5 mm/second to about 200 mm/second. It will be appreciated that the concentration of the polymer solutions may affect the drawing rate. In various embodiments, the polyanionic polymer solution has a polyanionic polymer concentration of from about 0.1% (w/v) to about 10% (w/v). In various embodiments, the polycationic polymer solution has a polycationic polymer concentration of from about 0.1% (w/v) to about 10% (w/v).

In various embodiments, the polyanionic polymer solution comprises one or more polyanionic polymer selected from the group consisting of natural and synthetic carbohydrate or polypeptide polymers having a net negative charge. In various embodiments, the polycationic polymer solution comprises one or more polycationic polymer selected from the group consisting of natural and synthetic carbohydrate or polypeptide polymers having a net positive charge. In one embodiment, the polyanionic polymer solution is sodium alginate and the polycationic polymer is chitosan or water-soluble chitin. In various embodiments, the polyanionic polymer and/or polycationic polymer are biodegradable and/or biocompatible. This allows the fibres to be suitable for use with living organisms such as cells.

In various embodiments, the method further comprises incorporating one or more biological material into the polyanionic polymer solution and/or polycationic polymer solution. The biological material may be encapsulated in the fibre as the fibre is being drawn from the polyelectrolyte complex interface. Alternatively, the biological material may be introduced by coating a drawn fibre with a layer of polyelectrolyte solution comprising a biological material. The coated layer of polyelectrolyte solution comprising the biological material may be encapsulated as additional fibres are formed over the coated layer. For example, the biological material may include edible materials such as animal and plant proteins, lipids, polysaccharides, dietary fibres, vitamins, minerals, cells and cellular components. In another example, the biological material may be selected from the group consisting of drugs, proteins, DNA, RNA, cells, viruses, microparticles, nanoparticles, contrast agents, and combinations thereof.

In various embodiments, there is provided a fibre construct comprising two or more fibres obtained using the method as disclosed herein. In various embodiments, there is provided a cell-fibre scaffold/construct comprising at least one fibre obtained using the method as disclosed herein. The cell-fibre scaffold/construct may provide a suitable structure which allows for three-dimensional tissue formation. In various embodiments, there is provided a food product comprising a plurality of fibres obtained using the method as disclosed herein. The food product may be an edible material-containing construct or a cell-containing construct such as clean meat (i.e. lab-grown, in vitro, or cultured meat) or a non-cell containing construct. For example, IPC fibres made from polyelectrolyte combinations of chitosan-alginate, chitosan-gellan and chitosan-poly(glutamic acid) may be useful for food product applications.

DETAILED DESCRIPTION OF FIGURES

Example embodiments of the disclosure will be better understood and readily apparent to one of ordinary skill in the art from the following discussions and if applicable, in conjunction with the figures. It should be appreciated that other modifications related to structural, chemical changes may be made without deviating from the scope of the invention. Example embodiments are not necessarily mutually exclusive as some may be combined with one or more embodiments to form new example embodiments.

Figure 1A:
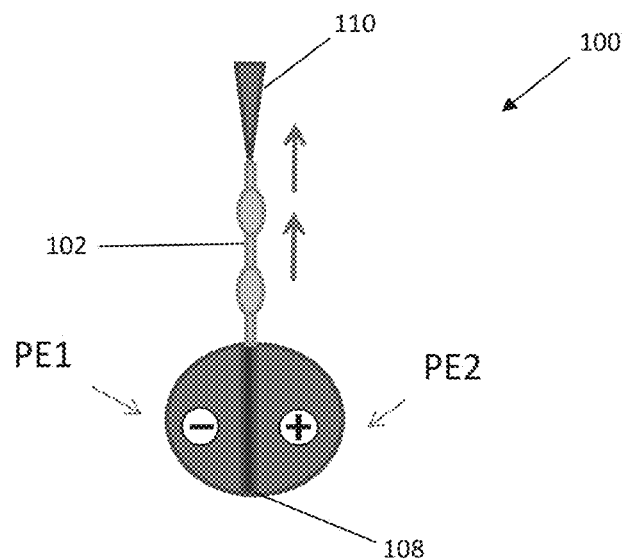
FIG. 1A is a schematic diagram showing a conventional IPC process of drawing a fibre in an example embodiment.
Figure 1B:
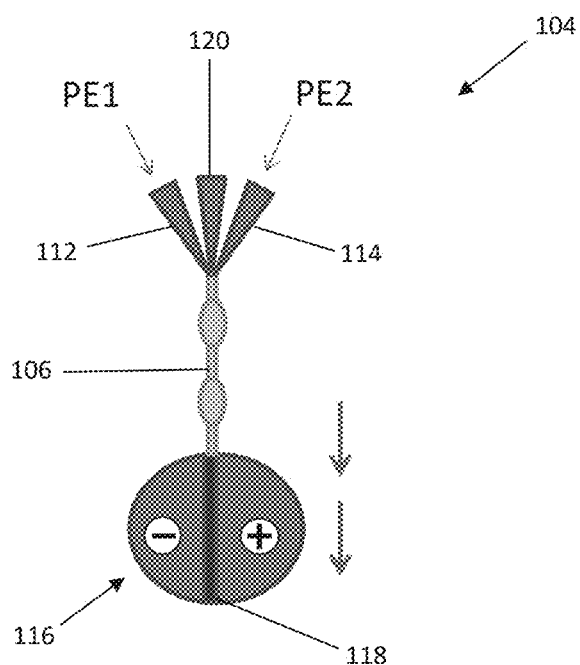
FIG. 1B is a schematic diagram showing a rolling droplet (RD)-IPC process of drawing a fibre in an example embodiment.

FIG. 1A is a schematic diagram showing a conventional IPC process 100 of drawing a fibre 102 in an example embodiment. FIG. 1B is a schematic diagram showing a rolling droplet (RD)-IPC process 104 of drawing a fibre 106 in an example embodiment.

In the conventional IPC process 100, a polyelectrolyte complex interface 108 is formed between a volume of an anionic polyelectrolyte solution (PE1) and a volume of a cationic polyelectrolyte solution (PE2). The fibre is drawn via upward movement (as indicated by the arrows) of a forceps or pipette tip 110 away from the polyelectrolyte complex interface 108. In other words, in the conventional IPC process 100, the polyelectrolyte complex interface 108 is in a substantially stationary position as the fibre 102 is being drawn.

In the RD-IPC process, a volume of an anionic polyelectrolyte solution (PE1) is dispensed from a first tip 112 and a volume of a cationic polyelectrolyte solution (PE2) is dispensed from a second tip 114. The volume of PE1 and the volume of PE2 are allowed to contact each other to form a fused droplet 116. The fused droplet 116 comprises a polyelectrolyte complex interface 118 separating the volume of PE1 and the volume of PE2. The fibre 106 is drawn as the polyelectrolyte complex interface 118 moves downwards (as indicated by the arrows) away from a point of attachment at the tips 112, 114, under the influence of gravity. In other words, in the RD-IPC process 104, the polyelectrolyte complex interface 108 is moving (i.e. falling downwards) as the fibre 106 is being drawn. A third tip 120 is provided between the first tip 112 and the second tip 114, with an adhesive substrate disposed at an apex region of the third tip 120 to facilitate coupling to a starting portion of the fibre 106. The adhesive substrate may also be provided on the first tip 112 and/or second tip 114 to facilitate coupling to a starting portion of the fibre 106.

Figure 2A:
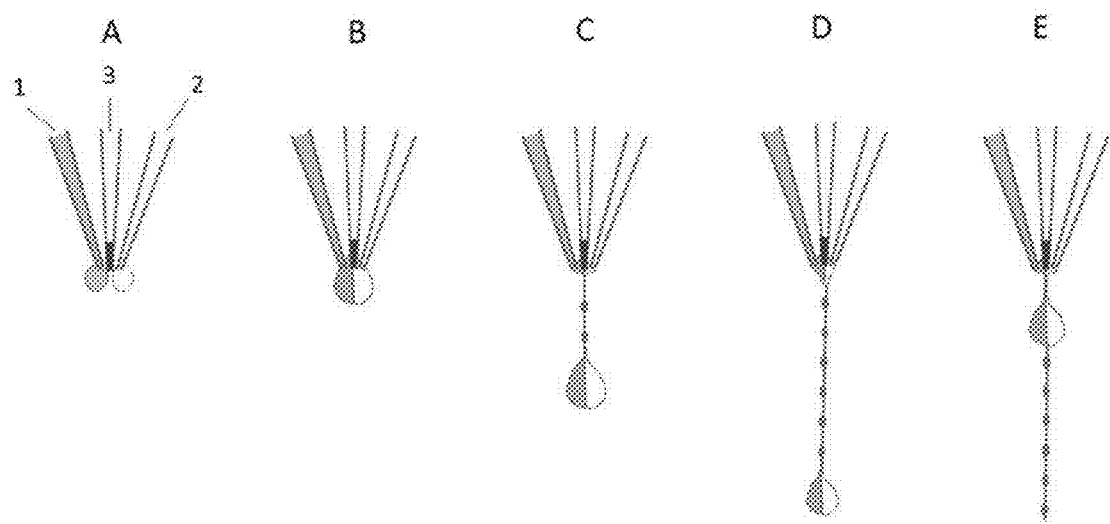
FIG. 2A is a schematic diagram showing a RD-IPC method of drawing IPC fibres in an example embodiment.

FIG. 2A is a schematic diagram showing a RD-IPC method of drawing IPC fibres in an example embodiment. The method relies on movement of a polyelectrolyte complex interface from a fixed point, in the form of a falling/ rolling droplet made up of the two oppositely charged polyelectrolytes (e.g. chitosan and sodium alginate). The general concept of RD-IPC is shown in FIG. 2A.

At step (A), using a syringe pump, two droplets of oppositely charged polyelectrolyte solutions are dispensed and brought together at a point via tubing terminating with pipette tips (1 and 2) that are positioned close to each other. A third tip in the middle (3) with a substrate at its apex region serves to support the growing fibre. At step (B), the two growing polyelectrolyte droplets at the end of the pipette tips (1 and 2) eventually come into contact and fuse to form a fused/combined droplet having a polyelectrolyte complex interface. Proceeding from step (B) to step (C), the fused/combined droplet gradually becomes larger. At step (C), when the fused droplet reaches a critical mass, it falls away by gravity from the point where the tips meet. At step (D), as nascent fibre is attached to the point where the two pipette tips meet (reinforced by the third tip), fibre is drawn as the droplet falls further away from the tips, while continuously being attached to the growing fibre. At step (E), if the polyelectrolyte solutions are continuously delivered to the tips, a second fused/combined droplet starts to form and eventually rolls down, forming a second fibre that fuses with the first initial fibre. In this way, continuous flow of the polyelectrolyte solutions results in the formation of more fused/combined droplets, which successively roll down the initial fibre, drawing more fibres in parallel to the first one. In this way, more fibres can be added to increase the thickness of the construct. Therefore, a construct comprising multiple fibres (>10) can be formed by allowing the process to continually occur till the desired construct size (thickness) is achieved.

Figure 2B:
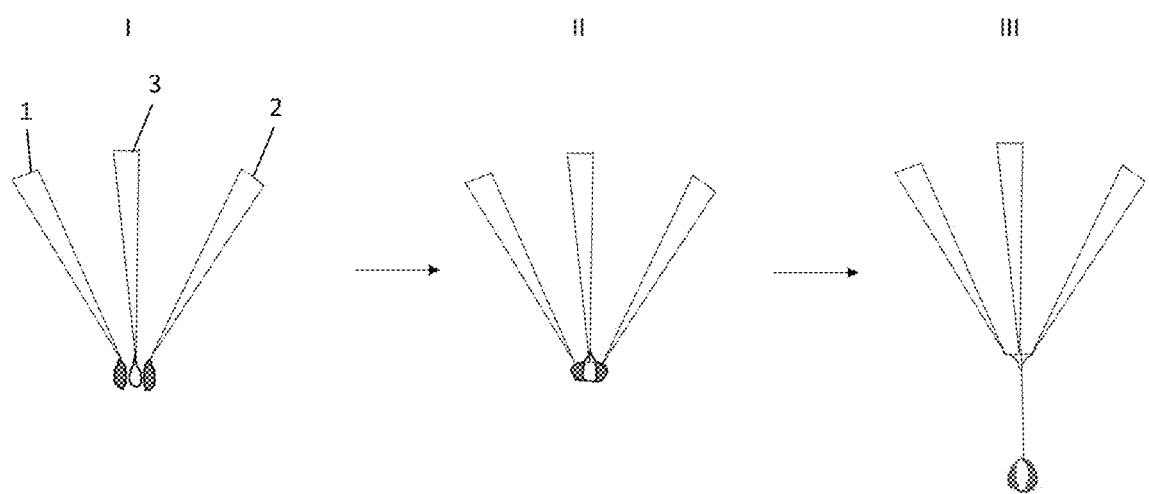
FIG. 2B is a schematic diagram showing a RD-MIPC method of drawing IPC fibres in an example embodiment.

FIG. 2B is a schematic diagram showing a RD-MIPC (rolling droplet-multi interfacial polyelectrolyte complexation) method of drawing IPC fibres in an example embodiment. The RD-MIPC method relies on movement of two or more polyelectrolyte complex interfaces away from a fixed point to form a multi-component fibre e.g. a two-component fibre. An example of the RD-MIPC method is shown in FIG. 2B for the case of two polyelectrolyte complex interfaces.

At step (I), using a syringe pump, three droplets of polyelectrolyte solutions are dispensed and brought together at a point via tubings terminating with pipette tips (1, 2 and 3) that are positioned close to one another. The droplet of polyelectrolyte solution dispensed from tip 3 (i.e. central droplet) has an opposite charge to the droplets of polyelectrolyte solutions dispensed from tips 1 and 2 (i.e. side/peripheral droplets). The polyelectrolyte solutions dispensed from tips 1 and 2 may comprise the same polyelectrolyte polymer or may comprise different polyelectrolyte polymers.

At step (II), the three growing polyelectrolyte droplets at the end of the pipette tips (1, 2 and 3) eventually come into contact and fuse to form a fused/combined droplet having two polyelectrolyte complex interfaces. That is, a first polyelectrolyte complex interface is formed between the polyelectrolyte polymer solutions dispensed from tips 1 and 3, and a second polyelectrolyte complex interface is formed between the polyelectrolyte polymer solutions dispensed from tips 2 and 3.

Proceeding from step (II) to step (III), the fused/combined droplet gradually becomes larger. When the fused droplet reaches a critical mass, it falls away by gravity from the point where the tips 1 to 3 meet. As nascent fibre is attached to the point where the three pipette tips meet, fibre is drawn as the droplet falls further away from the tips, while continuously being attached to the growing fibre. Similar to FIG. 2A, if the polyelectrolyte solutions are continuously delivered to the tips 1 to 3, a second fused/combined droplet may form and eventually roll down, forming a second fibre that fuses with the first initial fibre (see step (E) of FIG. 2A). In this way, continuous flow of the polyelectrolyte solutions results in the formation of more fused/combined droplets, which successively roll down the initial fibre, drawing more fibres in parallel to the first one. In this way, more fibres can be added to increase the thickness of the construct. Therefore, a construct comprising multiple fibres (>10) can be formed by allowing the process to continually occur till the desired construct size (thickness) is achieved.

Figure 2C:
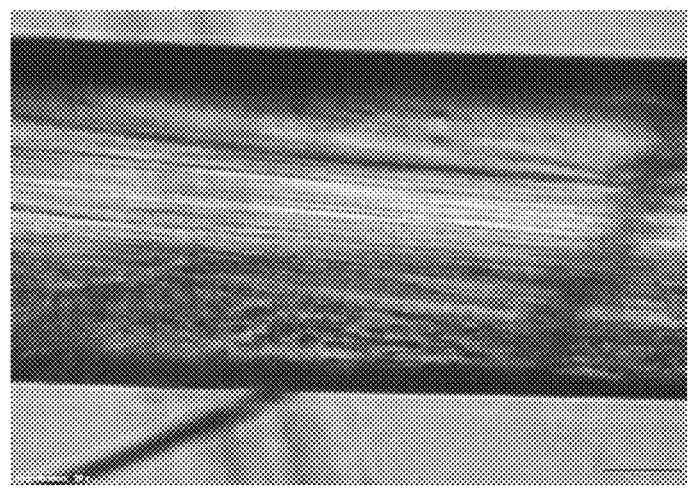
FIG. 2C is a microscope image of one example embodiment of a fibre construct consisting of multiple RD-IPC fibres obtained from the RD-IPC method. Scale bar=50 μm.
Figure 2D:
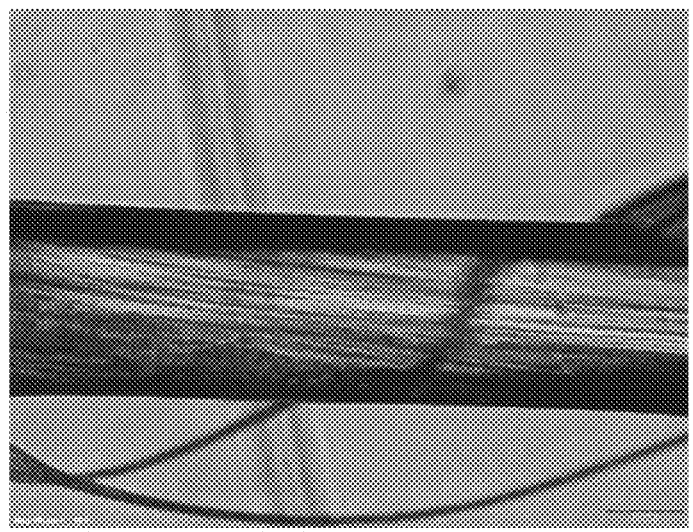
FIG. 2D is a microscope image of another example embodiment of a fibre construct consisting of multiple RD-IPC obtained from the RD-IPC method. Scale bar=100 μm.

FIG. 2C and FIG. 2D show example embodiments of a fibre construct consisting of multiple RD-IPC fibres obtained from the RD-IPC method of FIG. 2A. In the fibre construct as shown, multiple fibres are fused together to form a single fibre construct. The fibres formed using RD-IPC are typically fused together by collection to form the fibre construct, prior to drying. Thus, the protuberances due to gel droplets that are normally observed in a conventional IPC fibre may not be formed in the fibre construct obtained using RD-IPC.

EXAMPLES

Example embodiments of the disclosure will be better understood and readily apparent to one of ordinary skill in the art from the following examples, tables and if applicable, in conjunction with the figures.

Effect of Polyelectrolyte Concentrations on Fibre Thickness and Droplet Size

Figure 3A:
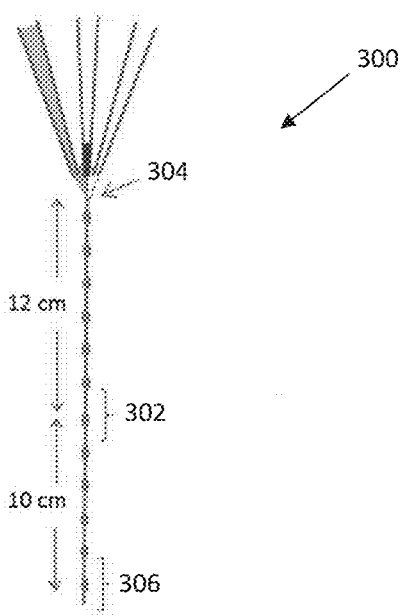
FIG. 3A is a schematic diagram showing measurement locations of the diameter of an IPC fibre in an example embodiment.
Figure 3B:
FIG. 3B is a photograph showing an actual experimental setup of a RD-IPC process in an example embodiment.

FIG. 3A is a schematic diagram showing measurement locations of the diameter of an IPC fibre 300 in an example embodiment. FIG. 3B is a photograph showing an actual experimental setup of a RD-IPC process in an example embodiment. It will be appreciated that the experimental setup of FIG. 3B is substantially based on the schematic diagram of FIG. 3A.

For each fibre, diameter measurements were made at a first location/upper segment 302 which is approximately 12 cm from the point of attachment 304 and at a second location/lower segment 306 further along the fibre, approximately 10 cm below the first location 302. This was performed to evaluate if there was a measurable decrease in thickness along the fibre, as the polyelectrolyte complex interface of the droplet is expected to decrease as it rolls downwards.

Figure 4A:
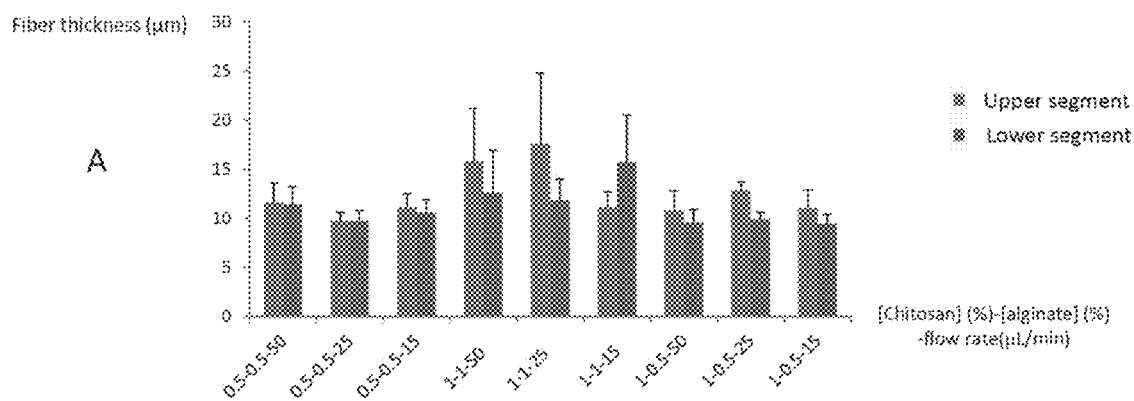
FIG. 4A is a graph showing fibre thickness measured at the first location and the second location for 1-fibre constructs obtained under different drawing conditions.
Figure 4B:
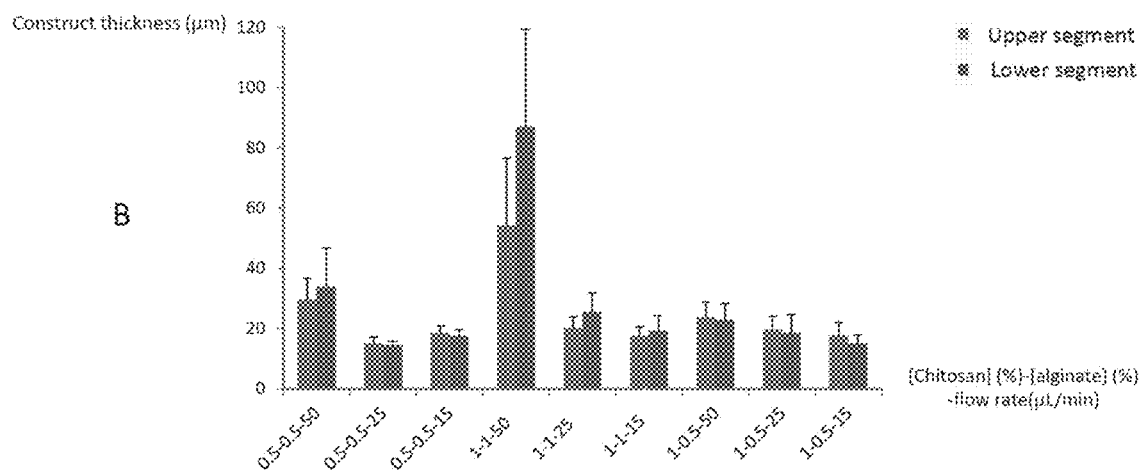
FIG. 4B is a graph showing fibre thickness measured at the first location and the second location for 3-fibre constructs obtained under different drawing conditions.
Figure 5A:
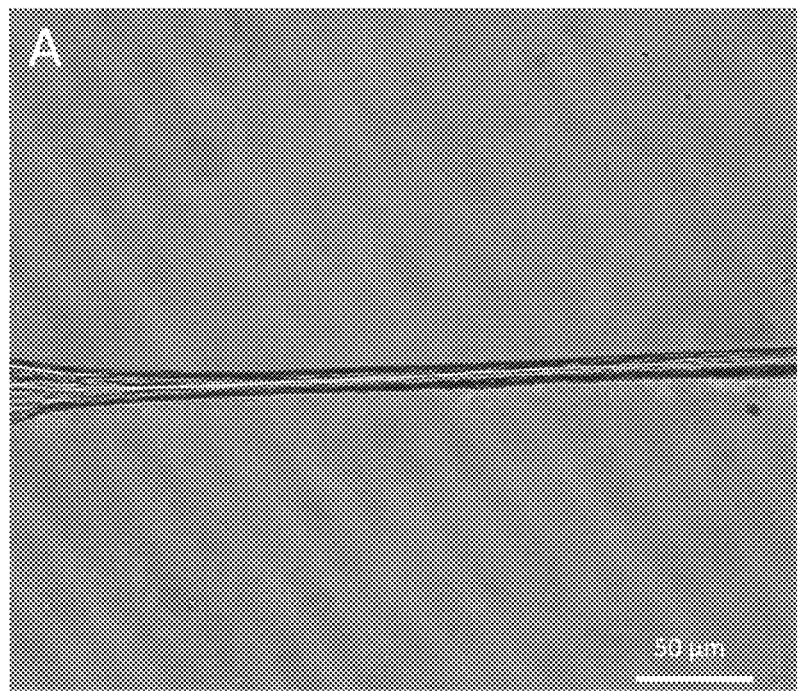
FIG. 5A is a microscope image of a 1-fibre construct drawn under conditions of 1% chitosan, 0.5% alginate and a flow rate of 25 μL/min. Scale bar=50 μm.
Figure 5B:
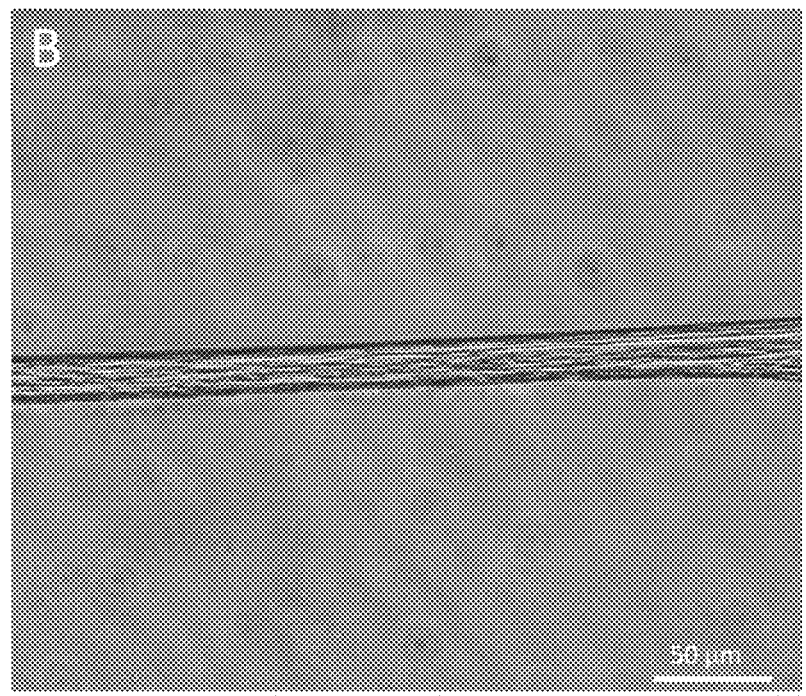
FIG. 5B is a microscope image of a 3-fibre construct drawn under conditions of 1% chitosan, 0.5% alginate and a flow rate of 25 μL/min. Scale bar=50 μm.

FIG. 4A is a graph showing fibre thickness measured at the first location and the second location for 1-fibre constructs obtained under different drawing conditions. FIG. 4B is a graph showing fibre thickness measured at the first location and the second location for 3-fibre constructs obtained under different drawing conditions. FIG. 5A is a microscope image of a 1-fibre construct drawn under conditions of 1% chitosan, 0.5% alginate and a flow rate of 25 µL/min. FIG. 5B is a microscope image of a 3-fibre construct drawn under conditions of 1% chitosan, 0.5% alginate and a flow rate of 25 µL/min. The 1-fibre and 3-fibre constructs were prepared using different polyelectrolyte concentrations and flow rates.

In general, there was no significant difference in thickness for the upper and lower fibre segments, except for the single fibres drawn using 1% chitosan and 0.5% alginate, where the upper segment was slightly thicker (see FIG. 4A). 3-fibre constructs drawn at a rate of 50 µL/min using 1% alginate and 1% chitosan were the thickest and exhibited the greatest variation in thickness. The higher thickness was due to nascent fibre being the most viscous and the short intervals that transpired between each successive drop.

There was a higher success rate for drawing of the 1% chitosan, 0.5% alginate 3-fibre construct. The latter condition avoided issues such as droplet not proceeding to the bottom, and breakage of fibre that occurred more frequently for the other combinations. Table 1 below shows the spread of fibre thicknesses under different conditions. Fibres obtained using 1% chitosan, 0.5% alginate showed relatively narrower spread in thicknesses for both the 1-fibre construct and 3-fibre constructs.

TABLE 1

Spread of fibre thicknesses under different conditions

| Polyelectrolyte concentrations (% w/v) | 1-fibre | 3-fibre |
|---|---|---|
| 0.5% chitosan, 0.5% alginate | 9-11 μm | 15-34 μm |
| 1% chitosan, 1% alginate | 11-16 μm | 18-87 μm |
| 1% chitosan, 0.5% alginate | 9-13 μm | 19-23 μm |
| 0.5% chitosan, 1% alginate | 9-14 μm | Not measured |

Rotary Collection of RD-IPC Fibres

The previous sections have described how successive droplets can be allowed to roll down existing IPC strands, thus accumulating multiple fibres. An alternative method to form thicker constructs would be to collect each fibre individually after it forms, whereupon it is accumulated on a collecting device.

Figure 6A:
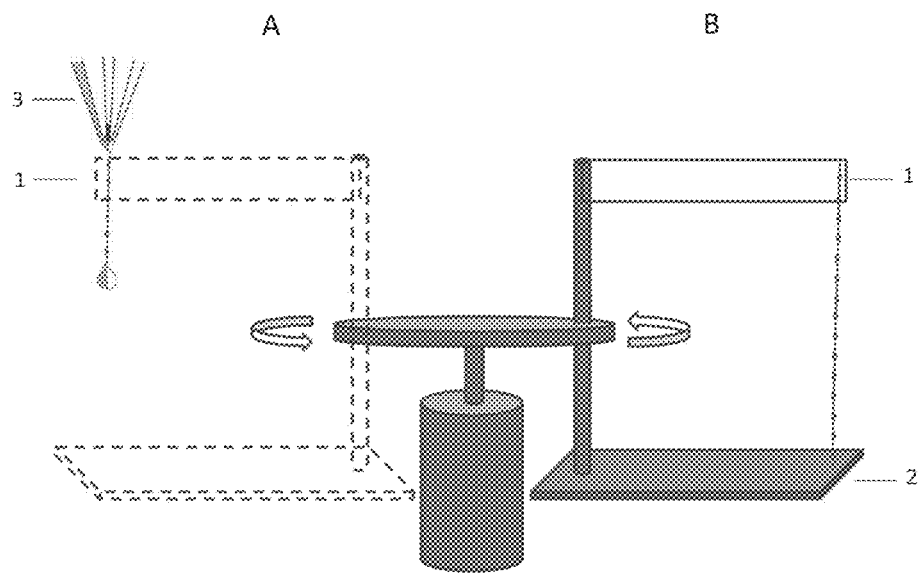
FIG. 6A is a schematic diagram showing rotary collection of RD-IPC fibres in an example embodiment.
Figure 6B:
FIG. 6B is a photograph showing an actual experimental setup of rotary collection of RD-IPC fibres in an example embodiment.

One such device configuration is shown in FIG. 6. FIG. 6A is a schematic diagram showing rotary collection of RD-IPC fibres in an example embodiment. FIG. 6B is a photograph showing an actual experimental setup of rotary collection of RD-IPC fibres in an example embodiment.

Referring to FIG. 6A, at position A, the collector (1), which is a rectangular piece of plastic, detaches a fibre from the pipette tips (3) due to its rotating motion. As the collector proceeds to rotate towards position B, the fibre increases in length due to the rolling droplet process. Eventually, the fibre attaches to the base plate (2) as the rolling droplet contacts the base plate (2). The collector then proceeds to rotate from position B to position A where a second fibre is deposited on the first, resulting in their combination. With each cycle, the construct grows in thickness by one fibre strand.

Figure 7A:
FIG. 7A is a photograph showing an RD-IPC fibre construct obtained via the rotary collection of approximately 80 fibre strands using 0.5% chitosan and 1% sodium alginate solutions.
Figure 7B:
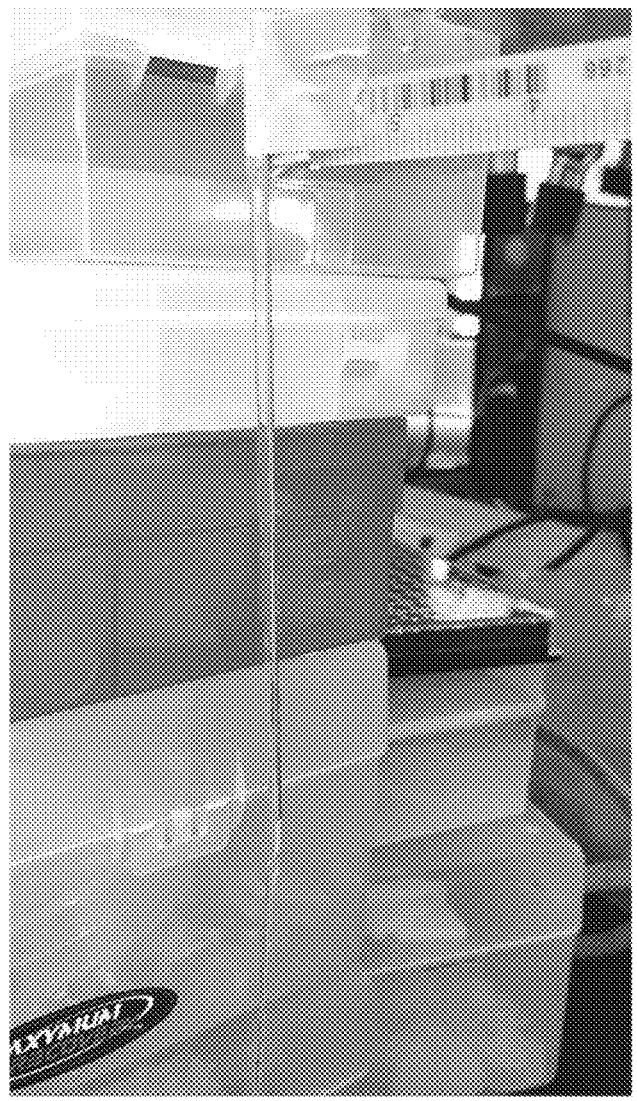
FIG. 7B is a photograph showing a guide member e.g. stainless-steel rod acting as a support for a fibre construct.
Figure 7C:
FIG. 7C is a photograph showing a relatively more uniform fibre obtained by including calcium ions in a polyelectrolyte solution.

FIG. 7A is a photograph showing an RD-IPC fibre construct obtained via the rotary collection of approximately 80 fibre strands using 0.5% chitosan and 1% sodium alginate solutions. FIG. 7B is a photograph showing a guide member e.g. stainless-steel rod acting as a support for a fibre construct. A metal support e.g. stainless-steel rod can be attached to the collector prior to collection of the fibres, whereby the accumulating RD-IPC fibres adhere to it (see FIG. 7B). To obtain a more uniform fibre, 25 mM Ca was included in the chitosan solution in the form of dissolved $CaCl_2$. FIG. 7C is a photograph showing a relatively more uniform fibre obtained by including calcium ions in a polyelectrolyte solution.

Encapsulation of Skeletal Muscle Cells in the Fibres

The IPC process takes place at room temperature and uses near-neutral pH solutions and is thus advantageous in terms of encapsulation of biological material such as proteins and cells. These advantages are equally relevant to RD-IPC. The collection of RD-IPC fibres by the rotary method as described in the previous section provides an additional method for the incorporation of biological material. This is illustrated by the incorporation of gelatin and skeletal muscle cells in the experiment described below.

Figure 8A:
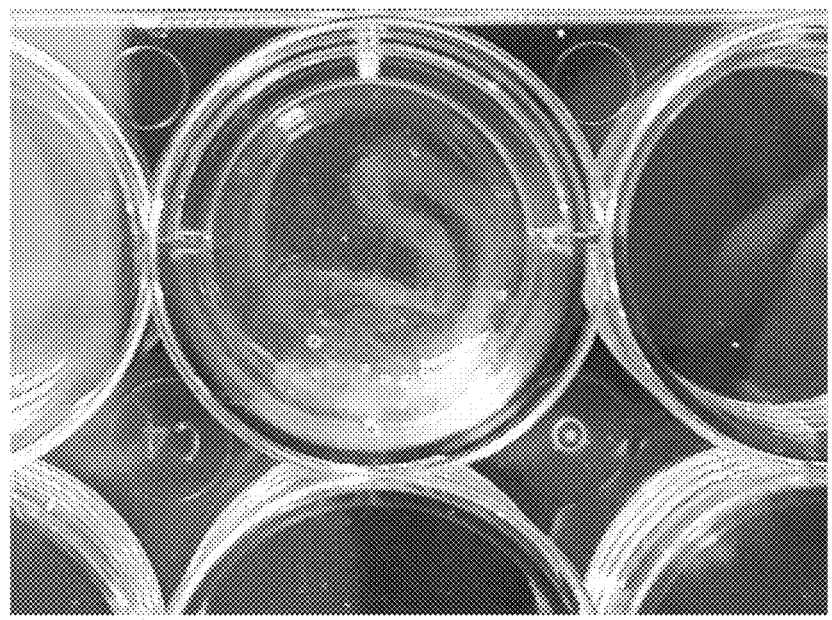
FIG. 8A is a photograph showing a culture of rotary-collected RD-IPC fibre construct in a 12-well culture plate.
Figure 8B:
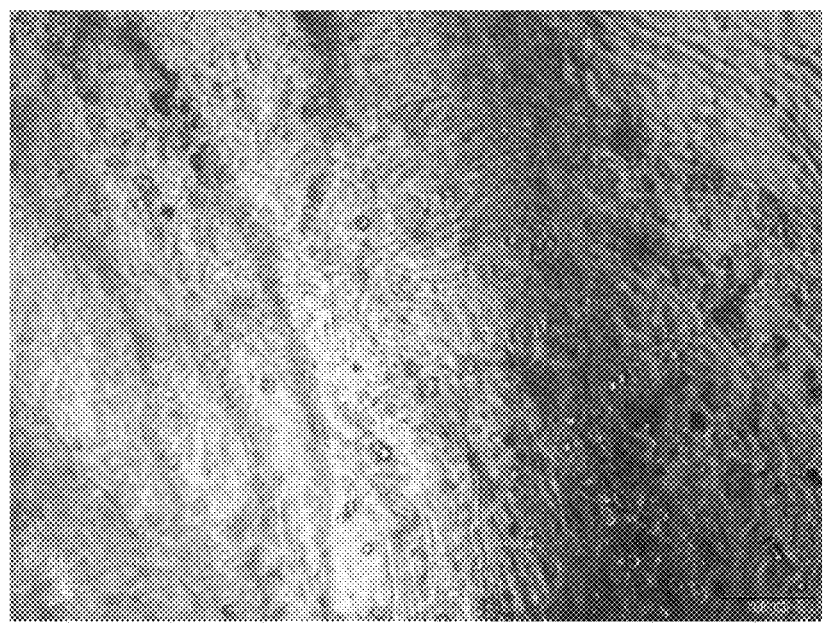
FIG. 8B is a bright-field microscope image of skeletal muscle cells in a fibre construct after 2 days of culture. Scale bar=200 µm.
Figure 8C:
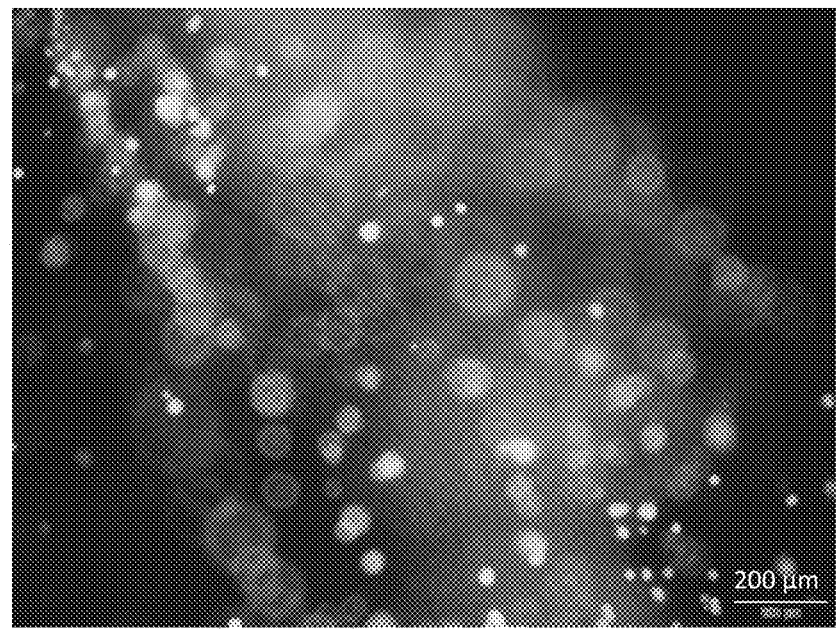
FIG. 8C is a corresponding fluorescent microscope image of the skeletal muscle cells stained with calcein (live) in the fibre construct after 2 days of culture. Scale bar=200 µm.
Figure 8D:
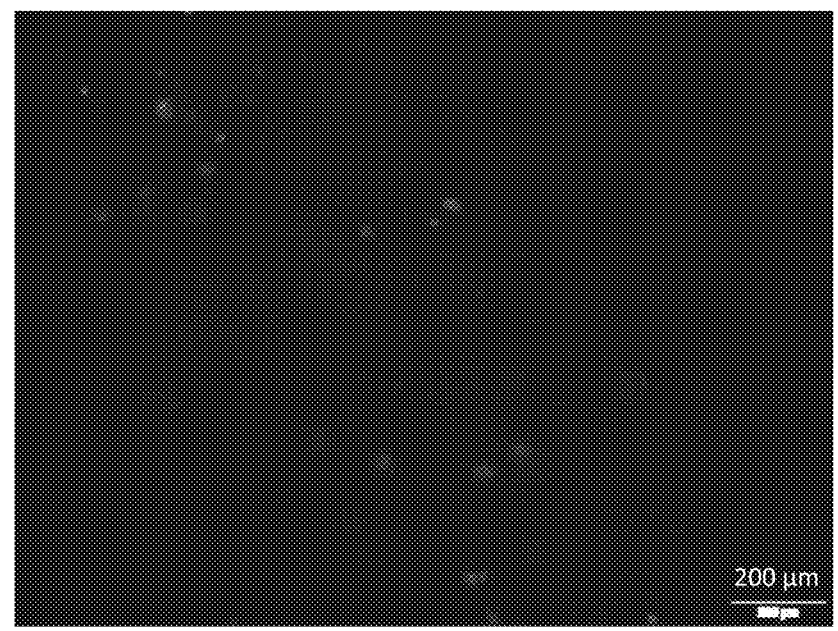
FIG. 8D is a corresponding fluorescent microscope image of the skeletal muscle cells stained with ethidium homodimer (dead) in the fibre construct after 2 days of culture. Scale bar=200 µm.

Rotary collection of RD-IPC fibres was performed as described in FIG. 6, using water soluble chitin as the polycation solution (1% w/v) and sodium alginate as the polyanion solution (1% w/v). After each cycle of RD-IPC fibre collection, the motor was stopped between positions A and B (see FIG. 6A). 20 μL of a suspension of $5\times10^5$ skeletal muscle cells in 5% w/v gelatin Type A was allowed to roll down the fibre, coating the fibre in the process. To optimise the coating, the viscosity of the latter solution could be tuned by changing its concentration or by incorporating an additional polyelectrolyte such as chitosan/water-soluble chitin. Approximately 80 droplets were used to form the construct. The resulting construct was detached from the pipette tips and placed in a 12-well culture plate containing skeletal muscle cell culture media (see FIG. 8A). After 2 days of culture, the cells were stained with a Live Dead Viability and Cytotoxicity Kit (Thermofisher) and observed under fluorescence. As shown in the microscope images of FIG. 8B to FIG. 8D, more than 90% of the cells were viable within the construct.

Production of RD-IPC Fibres in Series

For mass production of fibres and fibre constructs, it would be desirable to draw multiple fibres simultaneously. While this could be achieved by loading more syringes on a multi-syringe pump, for example, RD-IPC fibres can be produced in series via an alternative method.

Figure 9A:
FIG. 9A is a photograph showing production of RD-IPC fibres in series by dispensing oppositely charged polyelectrolyte solutions from tubes placed substantially parallel to each other in an example embodiment.
Figure 9B:
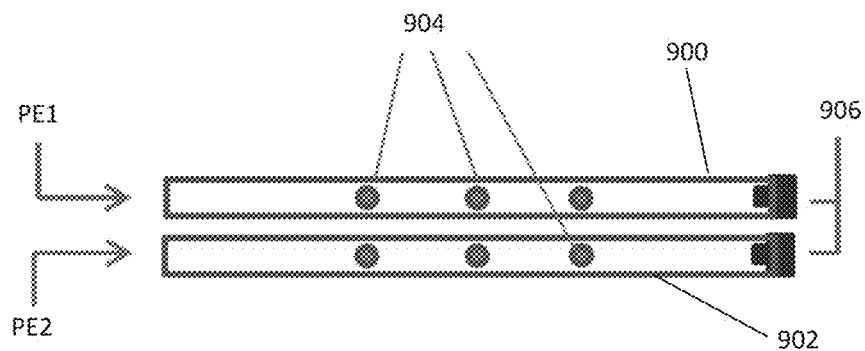
FIG. 9B is a schematic diagram showing production of RD-IPC fibres in series by dispensing oppositely charged polyelectrolyte solutions from tubes placed substantially parallel to each other in an example embodiment.
Figure 9C:
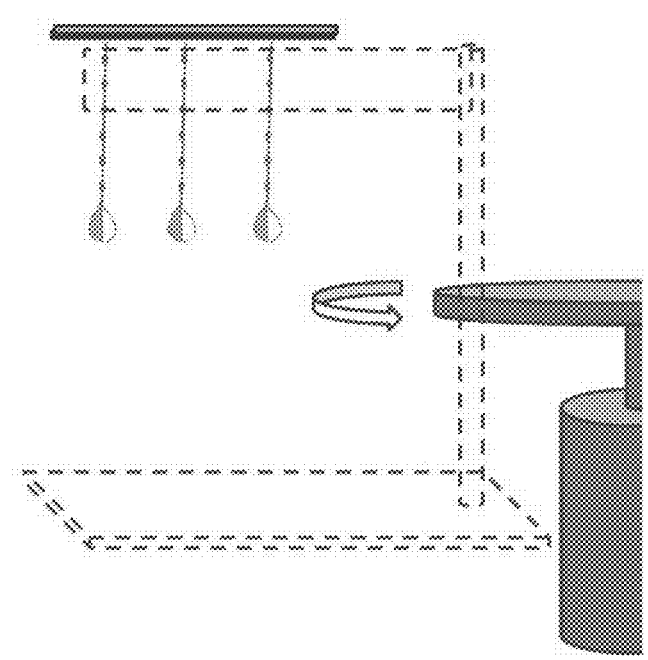
FIG. 9C is a schematic diagram showing production of RD-IPC fibres in series combined with rotary collection of RD-IPC fibres to form multiple fibre constructs in series in an example embodiment.

FIG. 9A is a photograph showing production of RD-IPC fibres in series by dispensing oppositely charged polyelectrolyte solutions from tubes placed substantially parallel to each other in an example embodiment. FIG. 9B is a schematic diagram showing production of RD-IPC fibres in series by dispensing oppositely charged polyelectrolyte solutions from tubes placed substantially parallel to each other in an example embodiment. FIG. 9C is a schematic diagram showing production of RD-IPC fibres in series combined with rotary collection of RD-IPC fibres to form multiple fibre constructs in series in an example embodiment.

Referring to FIG. 9B, two tubes (900, 902) are arranged to be fixed substantially parallel to each other. A series of perforations e.g. 904 is made on each tube to form holes in corresponding positions along their length. The pair of tubes 900, 902 comprise an open end for receiving the polyelectrolyte solutions (PE1, PE2) and a closed end sealed by stoppers 906. When oppositely charged polyelectrolytes (PE1, PE2) are dispensed through these tubes (900, 902), two or more RD-IPC fibres can be produced in series along the length of the tubes. This method can be combined with rotary collection of RD-IPC fibres (see FIG. 6) to form multiple fibre constructs in series (see FIG. 9C).

RD-IPC for Fibre Drawing/Cell Encapsulation in Water-Soluble Chitin (WSC)-RGD-Alginate Fibres Materials and Methods A 0.3% (w/v) WSC solution that had been dialysed using 14K MWCO dialysis membrane and filtered through 0.2 μm syringe filter was used for fibre drawing/cell encapsulation. RGD-alginate (RGD-A, Cellink) was diluted to obtain a ~3% (w/v) solution, which was added to a cell pellet containing $10^8$ C2C12 mouse myoblasts. The cells were resuspended by gentle tituration. A rectangular plastic "fibre-holder" measuring 8.5 cm×8.5 cm was employed for fibre collection. Cell encapsulation was performed in the laminar flow cabinet.

Figure 10A:
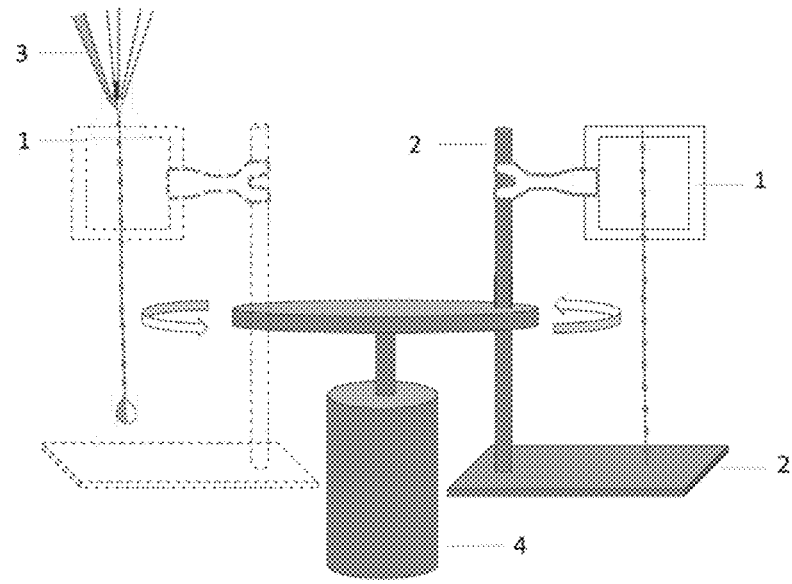
FIG. 10A is a schematic diagram showing rotary collection of RD-IPC fibres using square/rectangular fibre holders in an example embodiment.
Figure 10B:
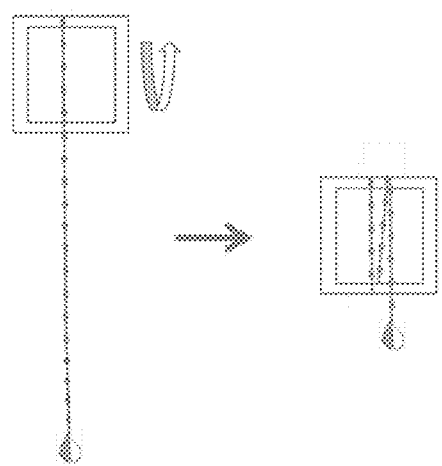
FIG. 10B is a schematic diagram showing spooling of RD-IPC fibres on the square/rectangular fibre holders in the example embodiment.

The setup for RD-IPC fibre drawing and spooling is shown in FIG. 10A and FIG. 10B. A square/rectangular piece of plastic in the shape of a frame (fibre-holder) (1) was clamped to the rod (2). The syringe pump was operated at a rate of 90 µL/min using 3 mL syringes containing WSC and RGD-alginate-cell suspension solutions, respectively. These solutions were dispensed via pipette tips (3) as illustrated in FIG. 10A. The rate of rotation for the fibre holder (controlled by motor (4)) was adjusted such that one fibre was collected for every rotation of the holder. Typically, approximately 1 mL of each solution was consumed to prepare one cell-fibre construct on the fibre-holder. The fibre-holder was removed from the clamp, and using a pair of forceps, the cell-fibre construct was spooled onto the holder (see FIG. 10B). The cell-fibre construct on holder was placed into a petri dish containing DMEM/10% FBS and cultured in the incubator.

Results

Figure 11A:
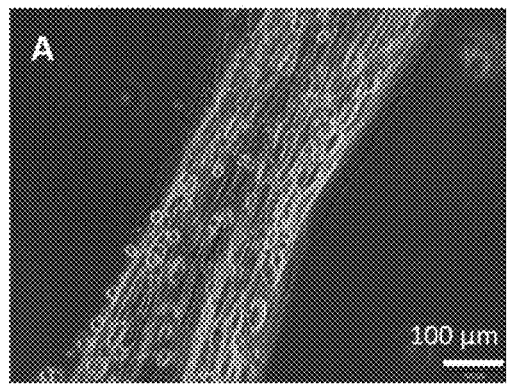
FIG. 11A is a bright-field microscope image for C2C12 mouse myoblasts in WSC-RGD-alginate RD-IPC fibres at 3 hours of culture. Scale bar=100 µm.
Figure 11B:
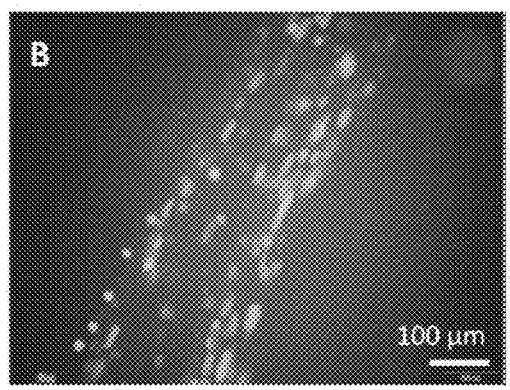
FIG. 11B is a corresponding fluorescent microscope image for the C2C12 mouse myoblasts stained with calcein (live) in the WSC-RGD-alginate RD-IPC fibres at 3 hours of culture. Scale bar=100 µm.
Figure 11C:
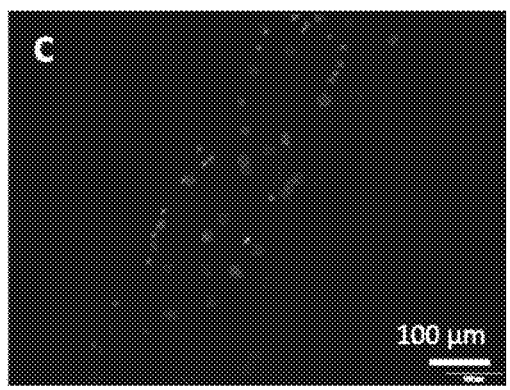
FIG. 11C is a corresponding fluorescent microscope image for the C2C12 mouse myoblasts stained with ethidium homodimer (dead) in the WSC-RGD-alginate RD-IPC fibres at 3 hours of culture. Scale bar=100 µm.
Figure 12:
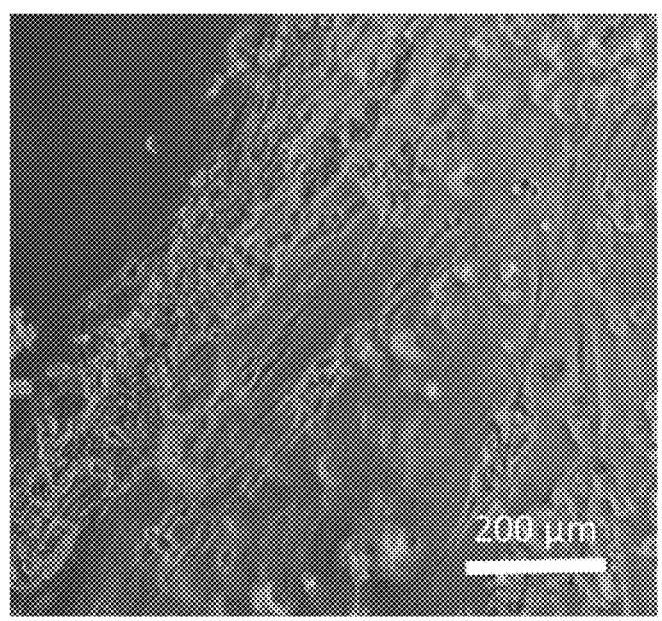
FIG. 12 is a light microscope image of C2C12 mouse myoblasts in WSC-RGD-alginate RD-IPC fibres after 24 hours of culture. Scale bar=200 µm.
Figure 13A:
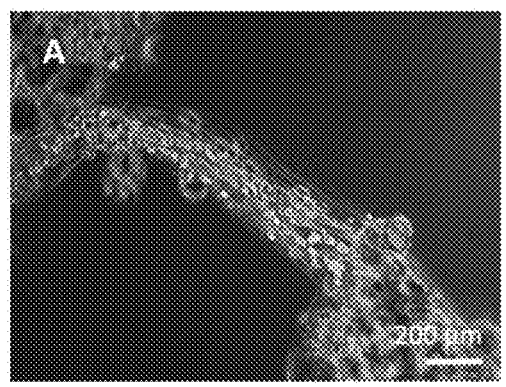
FIG. 13A is a bright-field microscope image for C2C12 mouse myoblasts in WSC-RGD-alginate RD-IPC fibres at 48 hours of culture. Scale bar=200 µm.
Figure 13B:
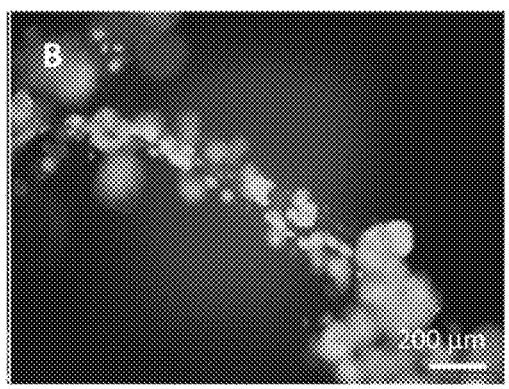
FIG. 13B is a corresponding fluorescent microscope image for the C2C12 mouse myoblasts stained with calcein (live) in the WSC-RGD-alginate RD-IPC fibres at 48 hours of culture. Scale bar=200 µm.
Figure 13C:
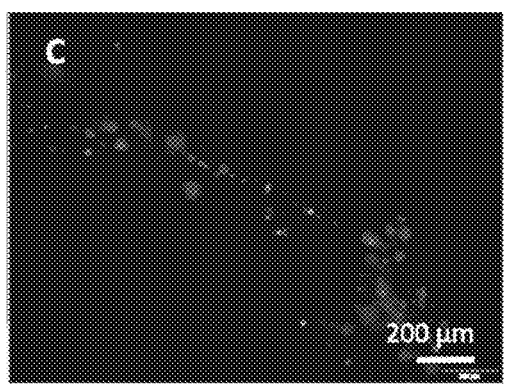
FIG. 13C is a corresponding fluorescent microscope image for the C2C12 mouse myoblasts stained with ethidium homodimer (dead) in the WSC-RGD-alginate RD-IPC fibres at 48 hours of culture. Scale bar=200 µm.
Figure 14A:
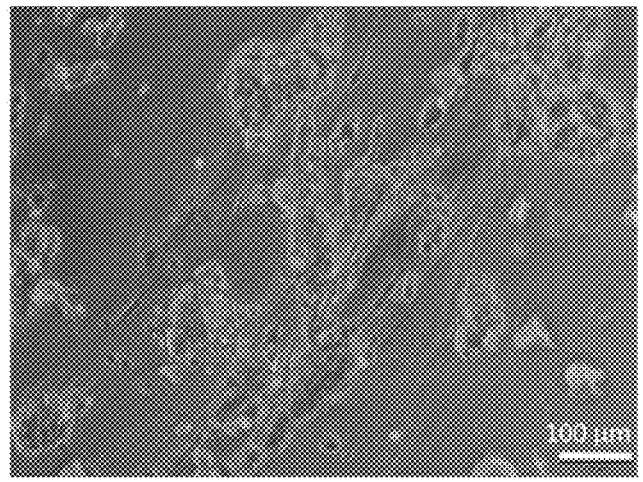
FIG. 14A is a first light microscope image of C2C12 mouse myoblasts in WSC-RGD-alginate RD-IPC fibres at 48 hours of culture. Scale bar=100 µm.
Figure 14B:
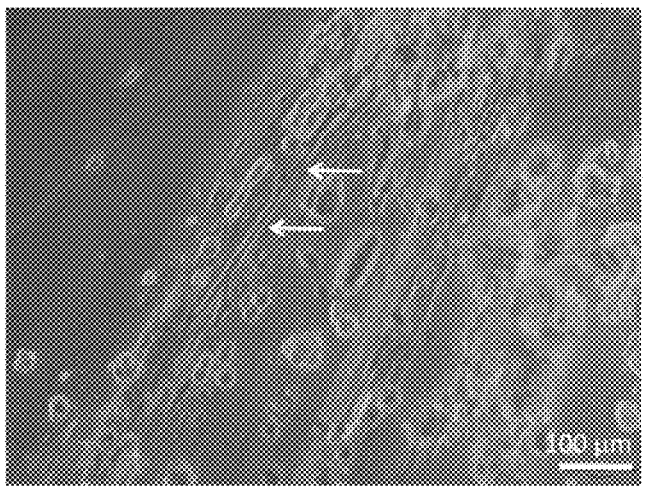
FIG. 14B is a second light microscope image of C2C12 mouse myoblasts in WSC-RGD-alginate RD-IPC fibres at 48 hours of culture. White arrows indicate spindle-shaped cells that formed connections with other cells. Scale bar=100 µm.

After 3 hours of culturing the fibre-cell constructs, the myoblasts exhibited good viability and showed some alignment along the fibre axis (see FIG. 11). The myoblasts demonstrated extensive alignment and spreading after 24 hours in culture, forming connections between the cells in some cases (see FIG. 12). After 48 hours in culture, the cells continued to exhibit good viability, however, most of the stained cells appeared as aggregates rather than spindle-shaped cells (see FIG. 13). Nevertheless, highly spread, spindle-shaped cells were still observed (see FIG. 14).

Assisted RD-IPC

Figure 15A:
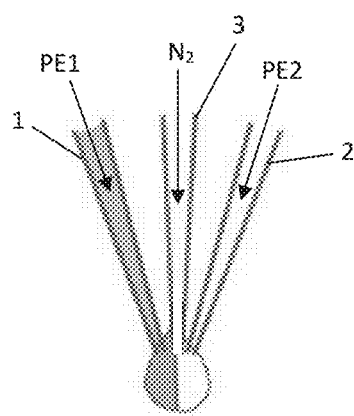
FIG. 15A is a schematic diagram showing an assisted RD-IPC where an additional tubing 3 is provided to deliver a stream of nitrogen gas between the polyelectrolyte solution dispensing tips 1 and 2 in an example embodiment.
Figure 15B:
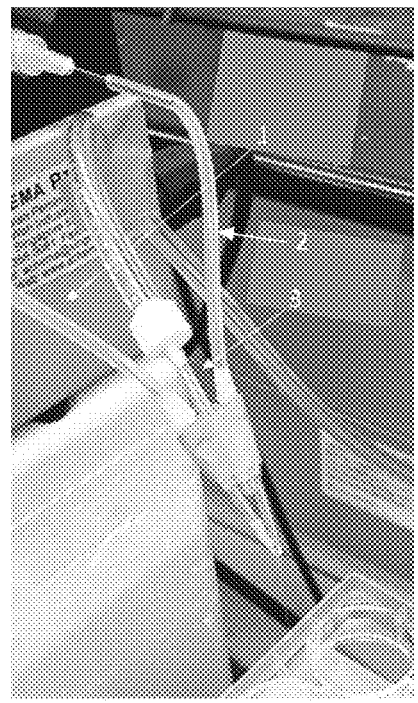
FIG. 15B is a photograph showing an actual experimental setup of an assisted RD-IPC where an additional tubing 3 is provided to deliver a stream of nitrogen gas between the polyelectrolyte solution dispensing tips 1 and 2 in an example embodiment.
Figure 15C:
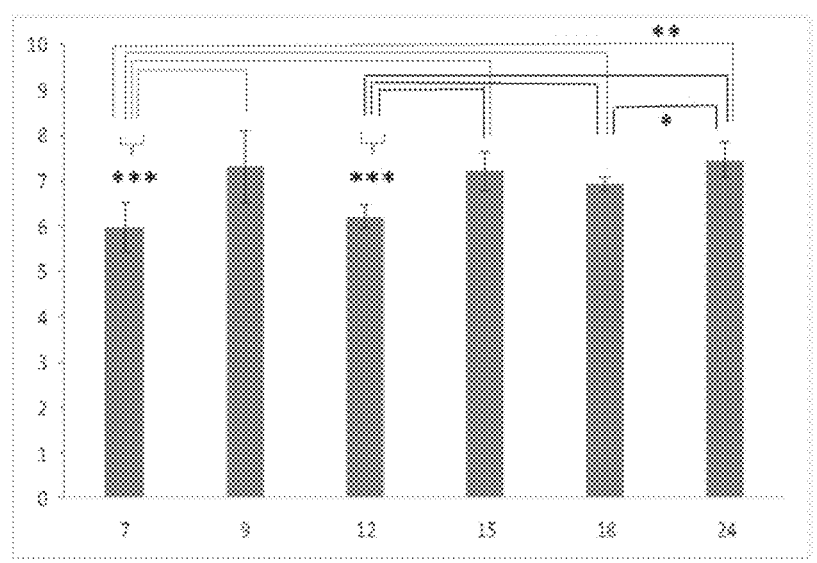
FIG. 15C is a graph showing a range of fibre diameters (Y-axis) obtainable by varying the time to drop (X-axis), $*p<0.05$, $p<0.005$, $*p<0.0005$.

In RD-IPC, the initial release of the droplet depends on its weight, as the droplet has to be sufficiently heavy to overcome its adhesion to the dispensing outlets e.g. pipette tips. Using various flow rates of a syringe pump (about 15, 25 and 50 µL/min) and the time taken for each droplet to fall for each flow rate, the average volume of the droplet was calculated to be about 40.3±2.2 µL (see Table 2). The inventors have recognized that the droplet size determines the size of the interface, which in turn determines the thickness of the fibre. Thicker fibres may be achieved by combining fibres or by using relatively more viscous solutions as described in the earlier sections. To tune fibre thickness for fibres with relatively smaller fibre diameters, a modified set-up (termed as "assisted RD-IPC") may be employed where a stream of nitrogen gas ($N_2$) is directed from an additional tubing (3) between the pipette tips (1, 2) dispensing polyelectrolyte solutions (PE1, PE2) fed via syringe pump(s), at appropriate timings/instances to dislodge the fused droplet (see FIGS. 15A and 15B). Using assisted RD-IPC, the droplet can be pushed away or dislodged from its attachment point before it achieves the critical weight to fall by gravity alone. In this way, smaller fibre diameters may be achievable, in particular, using drop times of 7 s and 12 s at a flow rate of 50 µL/min (see FIG. 15C).

TABLE 2

Calculation of droplet volumes from flow rate and average time to drop

| Syringe pump flow rate (µL/min) | Average time to drop (s) (n = 6) | Volume of droplet [2 × (time to drop/60) × flow rate] |
| --- | --- | --- |
| 50 | 24.7 ± 1.0 | 41.2 ± 1.7 |
| 25 | 46.5 ± 3.1 | 38.8 ± 2.6 |
| 15 | 81.8 ± 3.2 | 41.0 ± 1.6 |

Applications

Embodiments of the disclosure provided herein provide an apparatus and a method of drawing a fibre. In various embodiments, a fibre is drawn from a polyelectrolyte complex interface of a droplet which falls away by gravity from the point where two oppositely charged polyelectrolytes are dispensed and contacted. Fibre constructs can be made by allowing successive fibres to accumulate, or a rotating collector can be used to detach each fibre individually after it forms, whereupon it is accumulated on a collecting device.

Advantageously, various embodiments of the apparatus and method as disclosed herein rely on gravitational forces to draw fibres by virtue of a polyelectrolyte complex interface moving away from a stationary point where a starting portion of the fibre is attached. This is significantly different from conventional methods of drawing IPC fibres which involve drawing the nascent fibre away from a stationary polyelectrolyte complex interface. Various embodiments of the apparatus and method as disclosed herein provide an alternative method to draw fibres and to make fibre constructs by interfacial polyelectrolyte complexation which may be capable of being adapted into a continuous and scalable process for industrial applications such as those used in commercial product manufacture.

Even more advantageously, IPC fibres drawn using the apparatus and method as disclosed herein possess a unique, identifiable morphology. The fibres may be customised and applied in a wide variety of applications such as biomedical, pharmaceutical and food industries. For example, cell-fibre constructs or scaffolds formed using the apparatus and method as disclosed herein may be used for clean meat (i.e. lab-grown, in vitro, or cultured meat), drug testing and regenerative medicine (e.g. tissue engineering) applications. Fibre constructs or scaffolds formed using the apparatus and method as disclosed herein may also be used for non cell-containing constructs or edible material-containing constructs for food applications, where for example they could be used to modulate the texture of protein foods to a more fibrous-like constitution more closely resembling that of meat.

It will be appreciated by a person skilled in the art that other variations and/or modifications may be made to the embodiments disclosed herein without departing from the spirit or scope of the disclosure as broadly described. For example, in the description herein, features of different example embodiments may be mixed, combined, interchanged, incorporated, adopted, modified, included etc. or the like across different example embodiments. The present embodiments are, therefore, to be considered in all respects to be illustrative and not restrictive.

The invention claimed is:

1. An apparatus for drawing a fibre, the apparatus comprising, a first outlet for dispensing a volume of a first polyionic polymer solution;

a second outlet for dispensing a volume of a second oppositely charged polyionic polymer solution; said second outlet disposed adjacent to the first outlet such that the polymer solutions dispensed therefrom are capable of contacting each other to form a fused droplet comprising a polyelectrolyte complex interface separating the first polyionic and second polyionic polymer solutions;

a tip member disposed between, or in close proximity to, the first and second outlets for coupling to a starting portion of the fibre; and an adhesive substrate disposed at an apex region of the tip member to facilitate coupling to the starting portion of the fibre;
wherein the fused droplet is arranged to move along a fibre drawing path under gravitational force in an opposing direction from the first and second outlets such that nascent fibre is drawn from the polyelectrolyte complex interface.

2. The apparatus of claim 1, further comprising,
a gas outlet disposed between the first and second outlets, wherein the gas outlet is configured to discharge a stream of gas directed at the fused droplet to initiate movement of the fused droplet along the fibre drawing path.

3. The apparatus of claim 1, further comprising,
one or more pumps configured to continuously dispense the first and second polyionic polymer solutions via the respective first and second outlets to form additional fused droplets;
wherein the additional fused droplets are arranged to move along the fibre drawing path under gravitational force to form additional fibres.

4. The apparatus of claim 1, further comprising,
a rotatable collector member comprising a contact segment, said contact segment being configured to collect one or more fibres that are detachably coupled to the first and second outlets;
wherein the rotatable collector member is configured to rotate in a substantially horizontal plane such that the contact segment is arranged to collect the one or more fibres from the first and second outlets each time the contact segment passes in relation to the first and second outlets;
wherein the rotatable collector member is configured to collect and combine a plurality of fibres to form a fibre construct; and
optionally wherein the rotatable collector member is further configured to wind the fibre or fibre construct onto itself.

5. The apparatus of claim 4, further comprising,
an elongated guide member coupled to the rotatable collector member and arranged to be substantially aligned with the fibre drawing path, said elongated guide member configured to guide one or more fused droplets lengthwise along the elongated guide member.

6. The apparatus of claim 1, further comprising,
a first tube comprising a plurality of first outlets defined along a longitudinal axis of the first tube for dispensing a volume of the first polyionic polymer solution,
a second tube disposed substantially parallel to the first tube, said second tube comprising a plurality of second outlets defined along a longitudinal axis of the second tube for dispensing a volume of the second polyionic polymer solution;
wherein each of the plurality of first outlets is arranged to be disposed adjacent to a second outlet from the plurality of second outlets such that the polymer solutions dispensed therefrom are capable of contacting each other to form a plurality of fused droplets.

7. The apparatus of claim 1, further comprising,
the first and second outlets in the form of tapered tips;
wherein an adhesive substrate is disposed at apex regions of the tapered tips of the first and/or second outlets to facilitate coupling to the starting portion of the fibre.

8. The apparatus of claim 1, wherein the first and second polyionic polymers are selected from the following pairs of polycationic and polyanionic polymers consisting of chitosan-alginate, chitosan-heparin, poly(diallyldimethylammonium chloride)-poly(sodium 4-styrenesulfonate), chitosan-carboxymethylcellulose, water-soluble chitin-carboxymethylcellulose, chitosan-gellan and chitosan-poly (glutamic acid).

9. The apparatus of claim 1,
wherein the first and/or second polyionic polymer solutions further comprise a biological material;
optionally wherein the biological material is arranged to be encapsulated in the fibre as the fibre is being drawn from the polyelectrolyte complex interface; and
optionally wherein the biological material is selected from the group consisting of drugs, proteins, DNA, RNA, cells, viruses, microparticles, nanoparticles, contrast agents, and combinations thereof.

10. The apparatus of claim 1, further comprising,
a third outlet for dispensing a volume of a third polyionic polymer solution having an opposite charge to the second polyionic polymer solution;
wherein the third outlet is disposed adjacent to the second outlet such that the third polyionic polymer solution is capable of contacting the second polyionic polymer solution to form a second polyelectrolyte complex interface in the fused droplet; and
wherein a combined nascent fibre is drawn from the two polyelectrolyte complex interfaces as the fused droplet is arranged to move along the fibre drawing path.

11. A method of drawing a fibre, the method comprising,
dispensing a volume of a first polyionic polymer solution from a first outlet;
dispensing a volume of a second oppositely charged polyionic polymer solution from a second outlet, said second outlet being disposed adjacent to the first outlet;
contacting the volume of the first polyionic polymer solution and the volume of the second polyionic polymer solution to form a fused droplet comprising a polyelectrolyte complex interface separating the first polyionic and second polyionic polymer solutions;
coupling a starting portion of the fibre to a tip member disposed between, or in close proximity to, the first and second outlets, wherein an adhesive substrate is disposed at an apex region of the tip member to facilitate coupling to the starting portion of the fibre;
moving the fused droplet along a fibre drawing path under gravitational force in an opposing direction from the first and second outlets; and
drawing nascent fibre from the polyelectrolyte complex interface.

12. The method of claim 11, further comprising,
discharging a stream of gas from a gas outlet disposed between the first and second outlets, and
directing the stream of gas at the fused droplet to initiate movement of the fused droplet along the fibre drawing path.

13. The method of claim 11, further comprising,
continuously dispensing the first and second polyionic polymer solutions via the respective first and second outlets using one or more pumps to form additional fused droplets; and
moving the additional fused droplets along the fibre drawing path under gravitational force to form additional fibres.

14. The method of claim 11, further comprising,
rotating a rotatable collector member in a substantially horizontal plane;
collecting one or more fibres that are detachably coupled to the first and second outlets using a contact segment of the rotatable collector member each time the contact segment passes in relation to the first and second outlets;

combining a plurality of fibres to form a fibre construct;

optionally winding the fibre or fibre construct about the rotatable collector member; and optionally guiding one or more fused droplets lengthwise along an elongated guide member coupled to the rotatable collector member and arranged to be substantially aligned with the fibre drawing path.

15. The method of claim 11, further comprising, dispensing a volume of the first polyionic polymer solution from a plurality of first outlets defined along a longitudinal axis of a first tube;

dispensing a volume of the second polyionic polymer solution from a plurality of second outlets defined along a longitudinal axis of the second tube, said second tube disposed substantially parallel to the first tube;

contacting the volume of the first polyionic polymer solution dispensed from each of the plurality of first outlets with the volume of the second polyionic polymer solution from each of the plurality of second outlets to form a plurality of fused droplets.

16. The method of claim 11, further comprising, providing the first and second outlets in the form of tapered tips;

providing an adhesive substrate disposed at apex regions of the tapered tips of the first and/or second outlets to facilitate coupling to the starting portion of the fibre.

17. The method of claim 11, wherein the first and second polyionic polymers are selected from the following pairs of polycationic and polyanionic polymers consisting of chitosan-alginate, chitosan-heparin, poly(diallyldimethylammonium chloride)-poly (sodium 4-styrenesulfonate), chitosan-carboxymethylcellulose, water-soluble chitin-carboxymethylcellulose, chitosan-gellan and chitosan-poly (glutamic acid).

18. The method of claim 11, wherein the first and/or second polyionic polymer solutions further comprise a biological material;

optionally wherein the biological material is encapsulated in the fibre as the fibre is being drawn from the polyelectrolyte complex interface;

and optionally wherein the biological material is selected from the group consisting of drugs, proteins, DNA, RNA, cells, viruses, microparticles, nanoparticles, contrast agents, and combinations thereof.

19. The method of claim 11, further comprising, dispensing a volume of a third polyionic polymer solution from a third outlet disposed adjacent to the second outlet, said third polyionic polymer solution having an opposite charge to the second polyionic polymer solution and;

contacting the volume of the third polyionic polymer solution and the volume of the second polyionic polymer solution to form a second polyelectrolyte complex interface in the fused droplet; and drawing a combined nascent fibre from the two polyelectrolyte complex interfaces as the fused droplet is moving along the fibre drawing path.

20. An apparatus for drawing a fibre, the apparatus comprising, two or more outlets, each outlet configured for dispensing a volume of a polyionic polymer solution, a tip member disposed between, or in close proximity to, the two or more outlets for coupling to a starting portion of the fibre; and an adhesive substrate disposed at an apex region of the tip member to facilitate coupling to the starting portion of the fibre;

wherein the two or more outlets are arranged such that the polyionic polymer solutions dispensed therefrom are capable of contacting each other to form a fused droplet comprising at least one polyelectrolyte complex interface, each of the at least one polyelectrolyte complex interface separating two volumes of oppositely charged polyionic polymer solutions; and wherein the fused droplet is arranged to move along a fibre drawing path under gravitational force in an opposing direction from the two or more outlets such that nascent fibre is drawn from the at least one polyelectrolyte complex interface.

* * * * *